US008895510B2

(12) United States Patent  
Magnani

(10) Patent No.: US 8,895,510 B2  
(45) Date of Patent: Nov. 25, 2014

(54) PAN-SELECTIN INHIBITOR WITH ENHANCED PHARMACOKINETIC ACTIVITY

(75) Inventor: John L. Magnani, Gaithersburg, MD (US)

(73) Assignee: Glycomimetics, Inc., Gaithersburg, MD (US)

(*) Notice: Subject to any disclaimer, the term of this patent is extended or adjusted under 35 U.S.C. 154(b) by 1004 days.

(21) Appl. No.: 12/418,774

(22) Filed: Apr. 6, 2009

(65) Prior Publication Data

US 2009/0253646 A1 Oct. 8, 2009

Related U.S. Application Data

(60) Provisional application No. 61/123,571, filed on Apr. 8, 2008.

(51) Int. Cl.
  *A61K 31/7064* (2006.01)
  *C07H 15/22* (2006.01)
  *A61P 9/10* (2006.01)

(52) U.S. Cl.
  CPC ............ *C07H 15/22* (2013.01); *A61K 31/7064* (2013.01)
  USPC ........................................... 514/17.4; 536/35

(58) Field of Classification Search
  None
  See application file for complete search history.

(56) References Cited

U.S. PATENT DOCUMENTS

| | | | |
|---|---|---|---|
| 4,471,057 A | 9/1984 | Koprowski et al. ........... 436/518 |
| 4,599,203 A | 7/1986 | Conrow et al. | |
| 4,851,511 A | 7/1989 | Hakomori et al. ............ 530/387 |
| 4,859,769 A | 8/1989 | Karlsson et al. ................ 536/53 |
| 4,876,199 A | 10/1989 | Hakomori ..................... 530/387 |
| 4,925,796 A | 5/1990 | Bergh et al. ...................... 435/97 |
| 4,946,830 A | 8/1990 | Pulverer et al. .................. 514/23 |
| 5,143,712 A | 9/1992 | Brandley et al. ............... 424/1.1 |
| 5,151,360 A | 9/1992 | Handa et al. ............... 435/240.2 |
| 5,211,937 A | 5/1993 | Brandley et al. ............... 424/1.1 |
| 5,268,364 A | 12/1993 | Kojima et al. .................. 514/25 |
| 5,304,640 A | 4/1994 | Lasky et al. .................. 536/23.5 |
| 5,352,670 A | 10/1994 | Venot et al. ...................... 514/54 |
| 5,369,096 A | 11/1994 | Yamada et al. .................. 514/61 |
| 5,412,123 A | 5/1995 | Rao et al. ....................... 552/290 |
| 5,444,050 A | 8/1995 | Kogan et al. .................... 514/25 |
| 5,464,778 A | 11/1995 | Cummings et al. ........... 436/503 |
| 5,464,815 A | 11/1995 | Chamow et al. .................. 514/8 |
| 5,470,843 A | 11/1995 | Stahl et al. ....................... 514/61 |
| 5,484,891 A | 1/1996 | Lasky et al. ................. 530/387.3 |
| 5,486,536 A | 1/1996 | Ward et al. .................... 514/460 |
| 5,519,008 A | 5/1996 | Rao et al. ......................... 514/26 |
| 5,527,785 A | 6/1996 | Bevilacqua et al. ............. 514/56 |
| 5,538,724 A | 7/1996 | Butcher et al. .............. 424/152.1 |
| 5,559,103 A | 9/1996 | Gaeta et al. ...................... 514/54 |
| 5,576,305 A | 11/1996 | Ratcliffe ........................ 514/25 |
| 5,580,858 A | 12/1996 | Ippolito et al. .................. 514/25 |
| 5,580,862 A | 12/1996 | Rosen et al. ..................... 514/61 |
| 5,589,465 A | 12/1996 | Ishida et al. ..................... 514/25 |
| 5,604,207 A | 2/1997 | DeFrees et al. ................. 514/25 |
| 5,618,785 A | 4/1997 | Heavner et al. ................... 514/2 |
| 5,622,937 A | 4/1997 | Kogan et al. .................... 514/25 |
| 5,639,734 A | 6/1997 | Esko et al. ....................... 514/25 |
| 5,646,123 A | 7/1997 | Ippolito et al. .................. 514/25 |
| 5,646,248 A | 7/1997 | Sawada et al. ................ 530/350 |
| 5,648,344 A | 7/1997 | Brandley et al. ................ 514/61 |
| 5,654,282 A | 8/1997 | Tang et al. ....................... 514/25 |
| 5,654,412 A | 8/1997 | Srivastava et al. ........... 536/18.5 |
| 5,658,880 A | 8/1997 | Dasgupta et al. .................. 514/8 |
| 5,663,151 A | 9/1997 | Martel et al. .................... 514/25 |
| 5,679,321 A | 10/1997 | Dasgupta et al. .............. 424/9.1 |
| 5,679,644 A | 10/1997 | Rao et al. ......................... 514/26 |
| 5,686,426 A | 11/1997 | Martel et al. .................... 514/25 |
| 5,693,621 A | 12/1997 | Toepfer et al. ................... 514/25 |
| 5,695,752 A | 12/1997 | Rosen et al. ................. 424/94.61 |
| 5,710,023 A | 1/1998 | Collins et al. ................ 435/69.1 |
| 5,710,123 A | 1/1998 | Heavner et al. ................... 514/2 |
| 5,723,583 A | 3/1998 | Seed et al. .................. 530/387.3 |
| 5,728,685 A | 3/1998 | Abbas et al. ..................... 514/53 |
| 5,739,300 A | 4/1998 | Toepfer et al. .................. 536/4.1 |
| 5,747,463 A | 5/1998 | Marinier et al. ................. 514/25 |
| 5,750,508 A | 5/1998 | Dasgupta et al. ............... 514/25 |
| 5,753,617 A | 5/1998 | Heavner et al. ................... 514/9 |
| 5,753,631 A | 5/1998 | Paulson et al. .................. 514/25 |
| 5,763,413 A | 6/1998 | Numata et al. .................. 514/25 |
| 5,763,582 A | 6/1998 | Rao et al. .......................... 536/5 |
| 5,789,385 A | 8/1998 | Anderson et al. ............... 514/25 |
| 5,789,573 A | 8/1998 | Baker et al. .................. 536/24.5 |
| 5,795,958 A | 8/1998 | Rao et al. ....................... 530/331 |

(Continued)

FOREIGN PATENT DOCUMENTS

| | | |
|---|---|---|
| EP | 319253 A2 | 6/1989 |
| EP | 381310 A1 | 8/1990 |

(Continued)

OTHER PUBLICATIONS

Titz, A. et al "Mimetics of sialyl Lewis x . . . " Chimia (2007) vol. 61, pp. 194-197.*

Simanek, E. et al "Selectin-carbohydrate interactions . . . " Chem. Rev. (1998) vol. 98, pp. 833-862.*

Abraham, W.M. et al., "Selectin Blockade Prevents Antigen-induced Late Bronchial Response and Airway Hyperresponsiveness in Allergic Sheep," *Am J. Respir Crit Care Med.* 159: 1205-1214, 1999.

Acord, J. et al., "A rapid microplate method for quantifying inhibition of bacterial adhesion to eukaryotic cells," *Journal of Microbiological Methods* 60: 55-62, 2005.

Baeckström et al., "Purification and Characterization of a Membrane-bound and a Secreted Mucin-type Glycoprotein Carrying the Carcinoma-associated Sialyl-Le$^a$ Epitope on Distinct Core Proteins," *J. Biol. Chem.* 266(32):21537-21547, 1991.

Bänteli, R. et al., "Potent E-Selectin Antagonists," Helvetica Chimica Acta 83(11): 2893-2907, 2000.

(Continued)

*Primary Examiner* — Leigh Maier

(74) *Attorney, Agent, or Firm* — Ropes & Gray LLP

(57) ABSTRACT

Compounds, compositions and methods are provided for treatment of diseases or complications associated therewith, in which a selectin plays a role. More specifically, particular glycomimetics and uses thereof are described. For example, use of particular glycomimetics for treating sickle cell disease or a cancer involving a selectin, or complications associated with either, is described.

13 Claims, 9 Drawing Sheets

(56) References Cited

U.S. PATENT DOCUMENTS

| | | | |
|---|---|---|---|
| 5,811,404 A | 9/1998 | De Frees et al. | 514/25 |
| 5,811,405 A | 9/1998 | Toepfer et al. | 514/25 |
| 5,817,742 A | 10/1998 | Toepfer et al. | 528/328 |
| 5,827,817 A | 10/1998 | Larsen et al. | 514/2 |
| 5,827,837 A | 10/1998 | Bevilacqua et al. | 514/103 |
| 5,830,871 A | 11/1998 | Wong et al. | 514/23 |
| 5,837,689 A | 11/1998 | Anderson et al. | 514/25 |
| 5,837,690 A | 11/1998 | Rao et al. | 514/26 |
| 5,840,679 A | 11/1998 | Larsen et al. | 514/8 |
| 5,854,218 A | 12/1998 | DeFrees | 514/25 |
| 5,858,983 A | 1/1999 | Seed et al. | 514/23 |
| 5,858,994 A | 1/1999 | Kretzschmar et al. | 514/62 |
| 5,880,091 A | 3/1999 | Cummings et al. | 514/8 |
| 5,916,910 A | 6/1999 | Lai | 514/423 |
| 5,919,768 A | 7/1999 | Korgan et al. | 514/25 |
| 5,919,769 A | 7/1999 | Tsukida et al. | 514/25 |
| 5,962,422 A | 10/1999 | Nagy et al. | 514/25 |
| 5,976,540 A | 11/1999 | Rittershaus et al. | 424/184.1 |
| 5,977,080 A | 11/1999 | Rosen et al. | 514/25 |
| 5,985,852 A | 11/1999 | Nagy et al. | 514/54 |
| 5,994,402 A | 11/1999 | Rotstein et al. | 514/547 |
| 6,001,819 A | 12/1999 | Simon et al. | 514/54 |
| 6,001,988 A | 12/1999 | Parma et al. | 536/24.3 |
| 6,033,665 A | 3/2000 | Yednock et al. | 424/130.1 |
| 6,037,333 A | 3/2000 | Panjwani | 514/62 |
| 6,110,897 A | 8/2000 | Unverzagt et al. | 514/25 |
| 6,111,065 A | 8/2000 | Heavner et al. | 530/300 |
| 6,120,751 A | 9/2000 | Unger | 424/9.51 |
| 6,121,233 A | 9/2000 | Magnani et al. | 514/8 |
| 6,124,267 A | 9/2000 | McEver et al. | 514/25 |
| 6,133,239 A | 10/2000 | Handa et al. | 514/25 |
| 6,133,240 A | 10/2000 | Taylor et al. | 514/25 |
| 6,136,790 A | 10/2000 | Toepfer et al. | 514/25 |
| 6,169,077 B1 | 1/2001 | Oehrlein | 514/25 |
| 6,177,547 B1 | 1/2001 | Cummings et al. | 530/388.22 |
| 6,187,754 B1 | 2/2001 | Oehrlein | 514/25 |
| 6,193,973 B1 | 2/2001 | Tuttle | 424/195.1 |
| 6,193,979 B1 | 2/2001 | Rittershaus et al. | 424/195.11 |
| 6,197,752 B1 | 3/2001 | Schmidt et al. | 514/23 |
| 6,225,071 B1 | 5/2001 | Cummings et al. | 435/7.24 |
| 6,235,309 B1 | 5/2001 | Nagy et al. | 424/450 |
| 6,280,932 B1 | 8/2001 | Parma et al. | 435/6 |
| 6,309,639 B1 | 10/2001 | Cummings et al. | 424/143.1 |
| 6,387,884 B1 | 5/2002 | Magnani et al. | 514/25 |
| 6,391,857 B1 | 5/2002 | Magnani et al. | 514/25 |
| 6,407,135 B1 | 6/2002 | Lai et al. | 514/423 |
| 6,465,434 B1 | 10/2002 | Magnani et al. | 514/23 |
| 6,492,332 B1 | 12/2002 | Demopulos et al. | 514/12 |
| 6,503,885 B1 | 1/2003 | Kiso et al. | 514/25 |
| 6,528,487 B1 | 3/2003 | Heavner et al. | 514/13 |
| 7,060,685 B2 | 6/2006 | Magnani et al. | 514/25 |
| 7,728,117 B2 | 6/2010 | Magnani et al. | |
| 7,741,312 B2 | 6/2010 | Magnani et al. | |
| 7,989,601 B2 | 8/2011 | Magnani et al. | |
| 8,039,442 B2 | 10/2011 | Magnani et al. | |
| 2001/0046970 A1 | 11/2001 | Nagy et al. | 514/53 |
| 2001/0051370 A1 | 12/2001 | Bistrup et al. | 435/193 |
| 2002/0026033 A1 | 2/2002 | Cummings et al. | 530/322 |
| 2002/0028205 A1 | 3/2002 | Holgersson et al. | 424/184.1 |
| 2002/0031508 A1 | 3/2002 | Wagner et al. | 424/94.63 |
| 2002/0040008 A1 | 4/2002 | Wagner et al. | 514/41 |
| 2002/0132220 A1 | 9/2002 | Berens et al. | 435/1.1 |
| 2002/0164336 A1 | 11/2002 | Harrison et al. | 424/146.1 |
| 2002/0164748 A1 | 11/2002 | Bistrup et al. | 435/193 |
| 2002/0168366 A1 | 11/2002 | Stewart et al. | 424/146.1 |
| 2003/0012787 A1 | 1/2003 | Ashkenazi et al. | 424/145.1 |
| 2003/0012790 A1 | 1/2003 | Ashkenazi et al. | 424/178.1 |
| 2003/0018181 A1 | 1/2003 | Larsen et al. | 536/23.4 |
| 2003/0039683 A1 | 2/2003 | Cantrell et al. | 424/450 |
| 2004/0072796 A1 | 4/2004 | Embury et al. | |
| 2004/0219158 A1 | 11/2004 | Magnani | |
| 2005/0112124 A1 | 5/2005 | Frenette et al. | |
| 2005/0187171 A1 | 8/2005 | Magnani et al. | 514/43 |
| 2006/0217303 A1 | 9/2006 | Kriegler | |
| 2006/0287253 A1 | 12/2006 | Kriegler et al. | |
| 2007/0054870 A1 | 3/2007 | Magnani et al. | 514/35 |
| 2008/0112955 A1 | 5/2008 | Embury et al. | |
| 2008/0200406 A1 | 8/2008 | Magnani | |

FOREIGN PATENT DOCUMENTS

| | | |
|---|---|---|
| EP | 408859 B1 | 8/1995 |
| EP | 671407 A2 | 9/1995 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |
| WO | WO 94/29477 | 12/1994 |
| WO | WO 95/03059 | 2/1995 |
| WO | WO 95/29681 | 11/1995 |
| WO | WO 96/20204 | 7/1996 |
| WO | WO 96/25418 | 8/1996 |
| WO | WO 96/26950 | 9/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 99/42130 | 8/1999 |
| WO | WO 99/43353 | 9/1999 |
| WO | WO 99/43356 | 9/1999 |
| WO | WO 01/89564 | 11/2001 |
| WO | WO 02/22820 | 3/2002 |
| WO | WO 02/062810 | 8/2002 |
| WO | WO 03/088980 | 10/2003 |
| WO | WO 03/097658 | 11/2003 |
| WO | WO 2004/004636 | 1/2004 |
| WO | WO 2004/058304 | 7/2004 |
| WO | WO 2005/051920 | 6/2005 |
| WO | WO 2005/054264 | 6/2005 |
| WO | WO 2005/116088 | 12/2005 |
| WO | WO 2006/127906 | 11/2006 |
| WO | WO 2007/028050 | 3/2007 |
| WO | WO 2009/011889 | 1/2009 |
| WO | WO 2009/126556 | 10/2009 |

OTHER PUBLICATIONS

Belcher, J.D. et al., "Activated monocytes in sickle cell disease: potential role in the activation of vascular endothelium and vaso-occlusion," Blood, 96(7): 2451-2459, Oct. 1, 2000.

Belcher, J.D. et al., "Inflammatory Response in Transgenic Mouse Models of Human Sickle Cell Anemia," Abstract #2574, Blood, 96(11): 600a, Nov. 16, 2000.

Berg et al., "A Carbohydrate Domain Common to Both Sialyl Lea and Sialyl Lex is Recognized by the Endothelial Cell Leukocyte Adhesion Molecule ELAM-1," J. Biol. Chem. 266(23):14869-14872, 1991.

Berg et al., "The Cutaneous Lymphocyte Antigen is a Skin Lymphocyte Homing Receptor for the Vascular Lectin Endothelial Cell-Leukocyte Adhesion Molecule 1," J. Exp. Med. 174:1461-1466, 1991.

Bird and Kimber, "Oligosaccharides Containing Fucose Linked α(1-3) and α(1-4) to N-Acetylglucosamine Cause Decompaction of Mouse Morulae," Devel. Biol. 104:449-460, 1984.

Blanc-Muesser, et al., "Syntheses Stereoselective de 1-Thioglycosides," Carbohydrate Research 67:305-328, 1978.

Bock, K. et al., "Conformations in Solution of α,α-Trehalose, α-D-Glucopyranosyl α-D-Mannopyranoside, and Their 1-Thioglycosyl Analogs, and a Tentative Correlation of Their Behaviour with Respect to the Enzyme Trehalase," European Journal of Biochemistry 131:595-600, 1983.

Bowen et al., "Characterization of a Human Homologue of the Murine Peripheral Lymph Node Homing Receptor," Journal of Cell Biology 109:421-427, 1989.

Brandley et al., "Carbohydrate Ligands of LEC Cell Adhesion Molecules," Cell 63:861-863, 1990.

Broquet et al., "Effect of Desipramine on a Glycoprotein Sialyltransferase Activity in C6 Cultured Glioma Cells," J. Neurochem. 54:388-394, 1990.

Ceder, O. et al., "On the Absolute Configuration of 3-Cyclohexene-1-carboxylic Acid," Acta Chemica Scandinavica 24(8):2693-2698, 1970.

(56) References Cited

OTHER PUBLICATIONS

Chemical Abstracts (STN), Accession No. 1997:5843307, Jul. 8, 1997.
Childs et al., "High-molecular-weight glycoproteins are the major carriers of the carbohydrate differentiation antigens I, i and SSEA-1 of mouse teratocarcinoma cells," Biochem. J. 215:491-503, 1983.
Cleophax, J. et al., "A Chiral Synthesis of D-(+)-2,6-Dideoxystreptamine and its Microbial Incorporation into Novel Antibiotics," Journal of the American Chemical Society, 98(22): 7110-7112, Oct. 27, 1976.
Corral et al., "Requirements for Sialic Acid on Neutrophils in a GMP-140 (PADGEM) Mediated Adhesive Interaction with Activated Platelets," Biochem. Biophys. Res. Commun. 172:1349-1356, 1990.
Datta and Takayama, "Isolation and purification of trehalose 6-mono- and 6,6'-di-corynomycolates from *Cornyebacterium matruchotii*. Structural characterization of 1H NMR," Carbohydrate Research 245: 151-158, 1993.
Duijvestijn et al., "High Endothelial Differentiation in Human Lymphoid and Inflammatory Tissues Defined by Monoclonal Antibody HECA-452," Am. J. Path. 130:147-155, 1988.
Dupré, B. et al., "Glycomimetic Selectin Inhibitors: (α-D-Mannopyranosyloxy)methylbiphenyls," Bioorganic & Medicinal Chemistry Letters 6(5): 569-572, 1996.
Edgington, "How Sweet it is: Selectin-Mediating Drugs," Biotechnology 10: 383-389, 1992.
Eggens et al., "A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.
Eggens et al., "Specific Interaction between Lex and Lex Determinants. A Possible Basis for Cell Recognition in Preimplantation Embryos and in Embryonal Carcinoma Cells," J. Biol. Chem. 264(16):9476-9484, 1989.
Embury, S.H. et al., "The contribution of endothelial cell P-selectin to the microvascular flow of mouse sickle erythrocytes in vivo," Blood, 104(10): 3378-3385, Nov. 15, 2004.
Ernst and Oehrlein, "Substrate and donor specificity of glycosyl transferases," Glycoconjugate Journal 16: 161-170, 1999.
Fenderson et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al., "Coordinate Expression of X and Y Haptens during Murine Embryogenesis," Devel. Biol. 114:12-21, 1986.
Fenderson et al., "The blood group I antigen defined by monoclonal antibody C6 is a marker of early mesoderm during murine embryogenesis," Differentiation 38:124-133, 1988.
Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Fukushi et al., "Novel Fucolipids Accumulating in Human Adenocarcinoma. III. A Hybridoma Antibody (FH6) Defining a Human Cancer-Associated Difucoganglioside (VI3NeuAcV3III3Fuc2nLc6)," J. Biol. Chem. 259(16):10511-10517, 1984.
Gabius et al., "Endogenous Tumor Lectins: Overview and Perspectives," Anticancer Res. 6:573-578, 1986.
Gais, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al., "A cell-surface molecule involved in organ-specific homing of lymphocytes," Nature 304:30-34, 1983.
Gooi et al., "Stage-specific embryonic antigen involves α 1 → 3 fucosylated type 2 blood group chains," Nature 292:156-158, 1981.
Hakomori et al., "Novel Fucolipids Accumulating in Human Adenocarcinoma. I. Glycolipids With Di-or Trifucosylated Type 2 Chain," J. Biol. Chem. 259(7):4672-4680, 1984.
Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.

Hakomori S., "Aberrant Glycosylation in Cancer Cell Membranes as Focused on Glycolipids: Overview and Perspectives," Cancer Res. 45:2405-2414, 1985.
Handa et al., "Selectin GMP-140 (CD62; PADGEM) Binds to Sialosyl -Lea and Sialosyl-Lex, and Sulfated Glycans Modulate this Binding," Biochemical and Biophysical Research Communication 181(3):1223-1230, 1991.
Hansson and Zopf, "Biosynthesis of the Cancer-associated Sialyl-Lea Antigen," Journal of Biological Chemistry 260(16):9388-9392, 1985.
Harlan, John M., "Introduction: anti-adhesion therapy in sickle cell disease," Blood, 95(2): 365-367, Jan. 15, 2000.
Hasegawa et al., "Synthesis of deoxy-L-fucose-containing sialyl Lewis X ganglioside analogues," Carbohydrate Research 257: 67-80, 1994.
Hasegawa et al., "Synthesis of sialyl Lewis X ganglioside analogues containing modified L-fucose residues," Carbohydrate Research 274: 165-181, 1995.
Hebbel, R.P., "Blockade of Adhesion of Sickle Cells to Endothelium by Monoclonal Antibodies," The New England Journal of Medicine, 342(25): 1910-1912, Jun. 22, 2000.
Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.
Huse et al., "Generation of a Large Combinatorial Library of the Immunoglobulin Repertoire in Phage Lambda," Science 246:1275-1281, 1989.
Huwe, C.M. et al., "Design, Synthesis and Biological Evaluation of Aryl-substituted Sialyl Lewis X Mimetics Prepared Via Crossmetathesis of C-Fucopeptides," Biological & Medicinal Chemistry 7:773-788, 1999.
Hynes, R., "Integrins: A Family of Cell Surface Receptors," Cell 48:549-554, 1987.
Inwald, D.P. et al., "Platelet and leucocyte activation in childhood sickle cell disease: association with nocturnal hypoxaemia," British Journal of Haemotology, 111(2): 474-481, Nov. 2000.
Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.
Itai, S. et al., "Differentiation-dependent Expression of I and Sialyl I Antigens in the Developing Lung of Human Embryos and in Lung Cancers," Cancer Research 50: 7603-7611, 1990.
Jeffrey et al., "Affinity Chromatography of Carbohydrate-Specific Immunoglobulins: Coupling of Oligosaccharides to Sepharose ," Biochem. Biophys. Res. Commun. 62:608-613, 1975.
Jentsch, K.D. et al., "Inhibition of Human Immunodeficiency Virus Type I Reverse Transcriptase by Suramin-related Compounds," The Journal of General Virology 68(8): 2183-2192, 1987.
Kaila, N. et al., "Design and Synthesis of Sialyl Lewis Mimics as E- and P-Selectin Inhibitors," Medicinal Research Reviews, 22(6):566-601, 2002.
Kaila, N. et al., "β-C-Mannosides as Selectin Inhibtors," Journal of Medicinal Chemistry 45(8):1563-1566, 2002.
Kannagi et al., "New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.
Kannagi et al., "Stage-specific embryonic antigens (SSEA-3 and -4) are epitopes of a unique globo-series ganglioside isolated from human teratocarcinoma cells," Embo J. 2(12):2355-2361, 1983.
Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.
Kaul, D.K. et al., "Hypoxia/reoxygenation causes inflammatory response in transgenic sickle mice but not in normal mice," The Journal of Clinical Investigation, 106(3): 411-420, Aug. 2000.
Kitagawa et al., "Characterization of Mucin-Type Oligosaccharides With the Sialyl-Lea Structure From Human Colorectal Adenocarcinoma Cells," Biochem. Biophys. Res. Commun. 178(3):1429-1436, 1991.
Kitagawa et al., "Immunoaffinity Isolation of a Sialyl-Lea Oligosaccharide from Human Milk," J. Biochem. 104:591-594, 1988.

(56) References Cited

OTHER PUBLICATIONS

Kneuer, C. et al., "Selectins—potential pharmacological targets?" Drug Discovery Today, 11(21/22): 1034-1040, Nov. 2006.

Kogan, T.P. et al., "Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.

Kogan, T.P. et al., "Novel Synthetic Inhibitors of Selectin-Mediated Cell Adhesion: Synthesis of 1,6-Bis[3-(3-carboxymethylphenyl)-r-(2-α-D-monnopyranosyloxy)phenyl]hexane (TBC1269)," J. Med. Chem 41:1099-1111, 1998.

Kogan, T.P. et al., "Rational Design and Synthesis of Small Molecule, Non-oligosaccharide Selectin Inhibitors: (α-D-Mannopyranosyloxy)biphenyl-Substituted Corboxylic Acids," J. Med. Chem. 38: 4976-4984, Dec. 22, 1995.

Köhler and Milstein, "Continuous cultures of fused cells secreting antibody of predefined specificity," Nature 256:495-497, 1975.

Köhler and Milstein, "Derivation of specific antibody-producing tissue culture and tumor lines by cell fusion," Eur. J. Immunol. 6:511-519, 1976.

Kojima and Hakomori, "Specific Interaction between Gangliotriaosylceramide (Gg3) and Sialosyllactosylceramide (GM3) as a Basis for Specific Cellular Recognition between Lymphoma and Melanoma Cells," J. Biol. Chem. 264(34):20159-20162, 1989.

Kolb, H.C. et al., "Development of Tools for the Design of Selectin Antagonists," Chem. Eur. J. 3(10):1571-1578, 1997.

Kolb, H.C. et al., "Recent progress in the glycodrug area," Pure & Applied Chemistry 69(9):1879-1884, 1997.

Koprowski et al., "Colorectal Carcinoma Antigens Detected by Hybridoma Antibodies," Somatic Cell Genetics 5(6):957-972, 1979.

Kuzuoka, "Antitumor activity of murine monoclonal antibody NCC-ST-421," Chem. Ab. 115:27344v, 1991.

Lamblin et al., "Primary Structure Determination of Five Sialylated Oligosaccharides Derived from Bronchial Mucus Glycoproteins of Patients Suffering from Cystic Fibrosis. The Occurrence of the NeuAcα(2→3)Galβ(1→4)[Fucα(1→3)]GlcNAcβ(1→•) Structural Element Revealed by 500-Mhz H Nmr Spectroscopy," Journal of Biological Chemistry 259(14):9051-9058, 1984.

Larsen et al., PADGEM-Dependent Adhesion of Platelets to Monocytes and Neutrophils is Mediated by a Lineage-Specific Carbohydrate, LNF III (CD15), Cell 63:467-474, 1990.

Lindenberg et al., "Carbohydrate binding properties of mouse embryos," J. Reprod. Fert. 89:431-439, 1990.

Lipartiti et al., "Monosialoganglioside GM1 Reduces NMDA Neurotoxicity in Neonatal Rat Brain," Experimental Neurology 113:301-305, 1991.

Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.

Lowe et al., "ELAM-1-Dependent Cell Adhesion to Vascular Endothelium Determined by a Transfected Human Fucosyltransferase cDNA," Cell 63:475-484, 1990.

Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.

Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.

Magnani et al., "A Monoclonal Antibody-defined Antigen Associated with Gastrointestinal Cancer is a Ganglioside Containing Sialylated Lacto-N-fucopentaose II," Journal of Biological Chemistry 257(23):14365-14369, 1982.

Magnani, J., "Carbohydrate Sequences Detected by Murine Monoclonal Antibodies," Chemistry and Physics of Lipids 42:65-74, 1986.

Magnani, J., "Potent Glycomimetic Inhibitors of the Adhesion Molecule, PA-IIL, for the Bacterial Pathogen, *Pseudomonas auroginosa*," Glycobiology 13(11): 854, Abstract No. 104, Oct. 2003.

Matsui, N.M. et al., "Heparin inhibits the flow adhesion of sickle red blood cells to P-selectin," Blood, 100(10): 3790-3796, Nov. 15, 2002.

Matsui, N.M. et al., "P-selectin mediates the adhesion of sickle erythrocytes to the endothelium," Blood, 98(6): 1955-1962, Sep. 15, 2001.

Matsui, N.M. et al., "The Novel Adhesion of Erythrocytes to P-Selectin in Sickle Cell Disease," Abstract #2575, Blood, 96(11): 600a, Nov. 16, 2000.

Mulligan and Berg, "Selection for animal cells that express the *Escherichia coli* gene coding for xanthine-gunine phosphoribosyltransferase," Proc. Natl. Acad. Sci. USA 78:2072-2076, 1981.

Nagel, R.L., "A Knockout of a Transgenic Mouse—Animal Models of Sickle Cell Anemia," The New England Journal of Medicine, 339(3):194-195, Jul. 16, 1998.

Natarajan, M. et al., "Adhesion of Sickle Red Blood Cells and Damage to Interleukin-1β Stimulated Endothelial Cells Under Flow in Vitro," Blood, 87(11): 4845-4852, Jun. 1, 1996.

Nicolaou et al., "Total Synthesis of the Tumor-Associated Lex Family of Glycosphingolipids," J. Amer. Chem. Soc. 112:3693-3695, 1990.

Nudelman et al., "Novel Fucolipids of Human Adenocarcinoma: Disialosyl Lea Antigen (III4FucIII6NeuAcIV3NeuAcLc4) of Human Colonic Adenocarcinoma and the Monoclonal Antibody (FH7) Defining This Structure," J. Biol. Chem. 261:5487-5495, 1986.

Örhlein, R., "Carbohydrates and Derivatives as Potential Drug Candidates with Emphasis on the Selectin and Linear-B Area," Mini Reviews in Medicinal Chemistry 1: 349-361, 2001.

Palcic et al., "Enzymic Synthesis of Oligosaccharides Terminating in the Tumor-Associated Sialyl-Lewis-a Determinant," Carbohydr. Res. 190:1-11, 1989.

Palcic et al., "Regulation of N-Acetylglucosaminyltransferase V Activity. Kinetic Comparisons of Parental, Rous Sarcoma Virus-Transformed BHK, and L-Phytohemagglutinin-Resistant BHK Cells Using Synthetic Substrates and an Inhibitory Substrate Analog," J. Biol. Chem. 265:6759-6769, 1990.

Palcic et al., "A Bisubstrate Analog Inhibitor for α(1→2)-Fucosyltransferase," J. Biol. Chem. 264:17174-17181, 1989.

Palma-Vargas, J.M. et al., "Small-Molecule Selectin Inhibitor Protects Against Liver Inflammatory Response After Ischemia and Reperfusion," J. Am. Coll. Surg. 185: 365-372, 1997.

Patton, J.T. et al., "GMI-1070: a Small, Glycomimetic, Pan-selectin Antagonist that Improves Blood Flow and Inhibits Blood Cell Adhesion in Sickle Mice," Glyco XIX, Gaithersburg, Maryland, Sep. 2, 2005. Available from http://ww.glycomimetics.com/library. Accessed Jun. 10, 2009.

Perret, S. et al., "Structural basis for the interaction between human milk oligosaccharides and the bacterial lectin PA-IIL of *Pseudomonas aeruginosa*," Biochem. J. 389: 325-332, 2005.

Phillips et al., "ELAM-1 Mediates Cell Adhesion by Recognition of a Carbohydrate Ligand, Sialyl-Lex," Science 250:1130-1132, 1990.

Picker et al., "The Neutrophil Selectin LECAM-1 Presents Carbohydrate Ligands to the Vascular Selectins ELAM-1 and GMP-140," Cell 66:921-933, 1991.

Prokazova et al., "Sialylated lactosylceramides. Possible inducers of non-specific immunosuppression and atherosclerotic lesions," European Journal of Biochemistry 172:1-6, 1988.

Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.

Rice and Bevilacqua, "An Inducible Endothelial Cell Surface Glycoprotein Mediates Melanoma Adhesion," Science 246:1303-1306, 1989.

Ruoslahti and Pierschbacher, "New Perspectives in Cell Adhesion: RGD and Integrins," Science 238:491-497, 1987.

(56) References Cited

OTHER PUBLICATIONS

Sakurai et al., "Selection of a Monoclonal Antibody Reactive with a High-Molecular-Weight Glycoprotein Circulating in the Body Fluid of Gastrointestinal Cancer Patients," Cancer Research 48:4053-4058, 1988.
Sastry et al., "Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.
Scharfman, A. et al., "*Pseudomonas aeruginosa* binds to neoglycoconjugates bearing mucin carbohydrate determinants and predominantly to sialyl-Lewis x conjugates," Glycobiology 9(8): 757-764, 1999.
Scharfman, A. et al., "Recognition of Lewis x Derivatives Present on Mucins by Flagellar Components of *Pseudomonas aeruginosa*," Infection and Immunity 69(9): 5243-5248, Sep. 2001.
Shitara et al., "Application of Anti-Sialyl Lea Monoclonal antibody, KM231, for Immunotherapy of Cancer," Anticancer Res. 11:2003-2014, 1991.
Siuzdak et al., "Examination of the Sialyl Lewis X—Calcium Complex by Electrospray Mass Spectrometry," Bioorganic & Medicinal Chemistry Letters 4(24): 2863-2866, 1994.
Solovey, A. et al., "Circulating Activated Endothelial Cells in Sickle Cell Anemia," The New England Journal of Medicine, 337(22): 1584-1590, Nov. 27, 1997.
Solovey, AA., et al., "Modulation of endothelial cell activation in sickle cell disease: a pilot study," Blood, 97(7): 1937-1941, Apr. 1, 2001.
Sprengard, U. et al., "Synthesis and Biological Activity of Novel Sialyl-LewisX Conjugates," Bioorganic & Medicinal Chemistry Letters 6(5): 509-514, 1996.
Stanley and Atkinson, "The LEC11 Chinese Hamster Ovary Mutant Synthesizes N-Linked Carbohydrates Containing Sialylated, Fucosylated Lactosamine Units. Analysis by One- and Two-Dimensional H NMR Spectroscopy," J. Biol. Chem. 263(23):11374-11381, 1988.
Stephens and Cockett, "The construction of highly efficient and versatile set of mammalian expression vectors," Nucleic Acids Research. 17:7110, 1989.
Streeter et al., "Immunohistologic and Functional Characterization of a Vascular Addressin Involved in Lymphocyte Homing into Peripheral Lymph Nodes," Journal of Cell Biology 107: 1853-1862, 1988.
Stroud et al., "Extended Type 1 Chain Glycosphingolipids: Dimeric Lea (III4V4Fuc2Lc6) as Human Tumor-associated Antigen," J. Biol. Chem. 266(13):8439-8446, 1991.
Svenson and Lindberg, "Coupling of Acid Labile Salmonella Specific Oligosaccharides to Macromolecular Carriers," J. Immunol. Meth. 25:323-335, 1979.
Takada et al., "Adhesion of Human Cancer Cells to Vascular Endothelium Mediated by a Carbohydrate Antigen, Sialyl Lewis A1," Biochem. Biophys. Res. Commun. 179(2):713-719, 1991.
Takeichi, M., "Cadherins: a molecular family essential for selective cell-cell adhesion and animal morphogenesis," Trends Genet. 3(8):213-217, 1987.
Thoma, G. et al., "A readily Available, Highly Potent E-Selectin Antagonist," Angew. Chem. Int. Ed. 40(19): 3644-3647, 2001.
Thoma, G. et al., "Preorganization of the Bioactive Conformation of Sialyl LewisX Analogues Correlates with Their Affinity to E-Selectin," Angew. Chem. Int. Ed. 40(10): 1941-1945, 2001.
Thoma, G. et al., "Synthesis and Biological Evaluation of a Potent E-Selectin Antagonist," J. Med. Chem., 42: 4909-4913, 1999.
Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.
Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.
Trouet et al., "A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.
Turhan, A. et al., "Primary role for adherent leukocytes in sickle cell vascular occlusion: A new paradigm," Proceedings of the National Academy of Sciences, 99(5): 3047-3051, Mar. 5, 2002.
Tyrrell et al., "Structural requirements for the carbohydrate ligand of E-selectin," Proc. Natl. Acad. Sci. USA 88:10372-10376, 1991.
Waldmann, H. et al., "Synthesis of 2-Acetamindo-2-Deoxyglucosylasparagine Glyco-Tripeptide and—Pentapeptides by Selective C- and N-Terminal Elongation of the Peptide Chain," Carbohydrate Research 196: 75-93, 1990.
Walz et al., "Recognition by ELAM-1 of the Sialyl-Lex Determinant on Myeloid and Tumor Cells," Science 250:1132-1135, 1990.
Ward and Mulligan, "Blocking of adhesion molecules in vivo as anti-inflammatory therapy," Immunology 1: 165-171, 1994.
Whisler and Yates, "Regulation of Lymphocyte Responses by Human Gangliosides. I. Characteristics of Inhibitory Effects and the Induction of Impaired Activation," Journal of Immunology 125(5):2106-2111, 1980.
Yamazaki, F. et al., "Syntheisis of an appropriately protected core glycotetraoside, a key intermediate for the synthesis of 'bisected' complex-type glycans of a glycoprotein," Carbohydrate Research 201: 15-30, 1990.
Zhou et al., "The Selectin GMP-140 Binds to Sialylated, Fucosylated Lactosaminoglycans on Both Myeloid and Nonmyeloid Cells," Journal of Cell Biology 115(2):557-564, 1991.
Zopf et al., "Affinity Purification of Antibodies Using Oligosaccharide-Phenethylamine Derivatives Coupled to Sepharose," Meth. Enzymol. 50:171-175, 1978.
Bastin, R. et al, "Salt Selection and Optimisation Procedures for Pharmaceutical New Chemical Entities" Organic Process Research & Development (2000), vol. 4, pp. 427-435.
Bjercke, "Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Cao, X. et al., "Defective Lymphoid Development in Mice Lacking Expression of the Common Cytokine Receptor γ Chain," *Immunity* 2:223-238, Mar. 1995.
Christianson, S.W. et al., "Enhanced Human CD+ T Cell Engraftment in β₂-Microglobulin-Deficient NOD-*scid* Mice," *The Journal of Immunology* 158:3578-3586, 1997.
Ernst B. et al., "Design and Synthesis of E-Selectin Antagonists," *Chimia* 55:268-274, 2001.
Ishikawa, F. et al., "Chemotherapy-resistant human AML stem cells home to and engraft within the bone-marrow endosteal region," *Nature Biotechnology* 25(11): 1315-1321, Nov. 2007.
Lee et al., "A new method of sequencing linear oligosaccharides on gels using charged, fluorescent conjugates" Carbohydrate Research, vol. 214, 1991, pp. 155-168, XP000226749.
Li, B., et al., "Delaying Acute Graft-Versus-Host Disease in Mouse Bone Marrow Transplantation by Treating Donor Cells with Antibodies Directed at L-Selectin and α4-Integrin Prior to Infusion," Scand. J.,1 Immunol 59:464-468, 2004.
Payre, et al., "Chemoenzymatische Synthese eines zweifach modifizierten Pentasaccharids als Substrat fur einen alpha-Amylase-Assay durch Fluoreszenz-loschung" Angew. Chem., vol. 107, No. 11, 1995, pp. 1361-1364.
Stevenson, J. et al., "Differential metastasis inhibition by clinically relevant levels of heparins . . . " Clin. Cancer Res. (2005) vol. 11, No. 19, pp. 7003-7011.
Vlodavsky, I. et al., "Heparanase, heparin and the coagulation system . . . " Thromb. Res. (2007) vol. 120, suppl. 2, pp. S112-S120.
Bueltmann et al., "P2-Purinoceptor Antagonists: III. Blockade of P2-Purinoceptor Subtypes and Ecto-Nucleotidases by Compounds Related to Suramin," Naunyn-Schmiedeberg's Archives of Pharmacology, Springer, DE, vol. 354, No. 4, Oct. 1, 1996, pp. 498-504, XP009078852.

\* cited by examiner

PAN-SELECTIN INHIBITOR WITH ENHANCED PHARMACOKINETIC ACTIVITY

CROSS-REFERENCE TO RELATED APPLICATION

This application claims the benefit under 35 U.S.C. §119(e) of U.S. Provisional Patent Application No. 61/123,571 filed Apr. 8, 2008; which application is incorporated herein by reference in its entirety.

BACKGROUND

1. Technical Field

The present invention relates generally to compounds, compositions and methods for treating diseases or complications associated therewith, in which a selectin plays a role such as sickle cell disease or a cancer involving a selectin. More specifically, the present invention relates to particular glycomimetics and uses thereof.

2. Description of the Related Art

Selectins play, and are being discovered to play, a role in a variety of diseases and complications associated therewith. Inhibitors of selectins may be used to treat such diseases or complications.

Sickle cell disease is an inheritable hematological disorder based on a mutation in the β-globin gene of hemoglobin. Upon deoxygenation, this mutated hemoglobin polymerizes and causes a shape change (sickling) of the red blood cell. This change in red blood cells leads to obstruction of blood vessels causing a wide variety of complications such as stroke, pulmonary hypertension, end-organ disease and death.

In addition to the fatal or potentially fatal complications, there are serious non-fatal complications of sickle cell disease such as pain. The severity of the pain may vary, but normally requires some form of medical attention. Hospitalization may be necessary.

In the U.S. alone, approximately 70,000-80,000 people suffer from sickle cell disease. Sickle cell disease is estimated to affect one of every 1,300 infants in the general population, and one of every 400 of African descent. Currently, there is no cure for sickle cell disease. The disease is chronic and life-long. Life expectancy is typically shortened.

Accordingly, there is a need in the art for the treatment of sickle cell disease or the complications associated therewith. The present invention fulfills these needs and further provides other related advantages.

BRIEF SUMMARY

Briefly stated, compounds, compositions and methods for treating diseases or complications associated therewith, in which a selectin plays a role, are provided. In the present invention, the compounds used for treatment are particular glycomimetics. Such compounds may be combined with a pharmaceutically acceptable carrier or diluent to form a pharmaceutical composition. The present compounds are inhibitors of selecting. Such compounds may be used to treat a variety of diseases or complications associated therewith, including sickle cell disease, a disease involving the migration of T-cells to the skin, acute myocardial infarction, or a cancer involving a selectin.

In one embodiment, the present invention provides a compound having the formula:

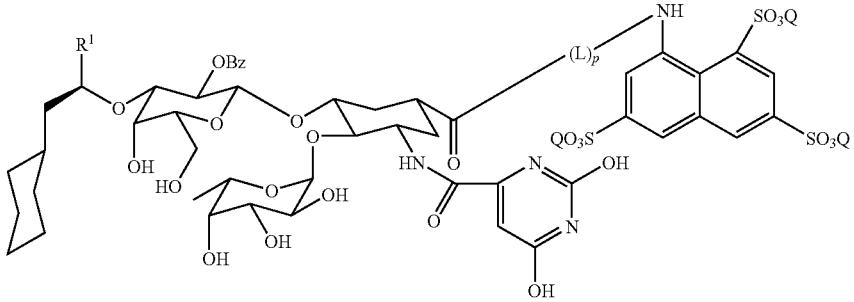

wherein
Bz=benzoyl;
Q is H or a physiologically acceptable salt;
L=linker group;
p=0-1; and
$R^1$ is one of

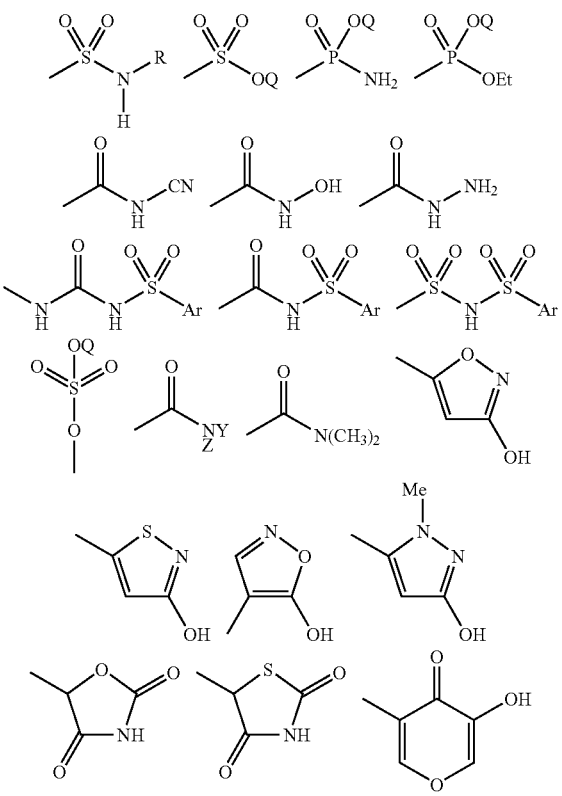

-continued

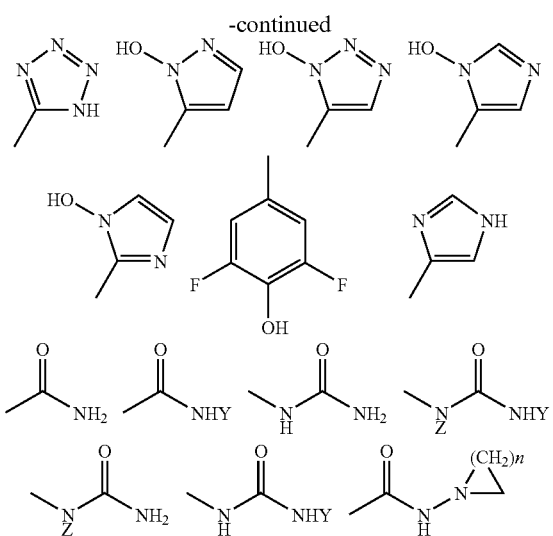

where Ar is aryl, Q is H, a physiologically acceptable salt, $C_1$-$C_8$ alkanyl, $C_1$-$C_8$ alkenyl, $C_1$-$C_8$ alkynyl, aryl, or $(CH_2)_m$-aryl where m is 1-10, n=1-4, and Z and Y are independently selected from $C_1$-$C_8$ alkanyl, $C_1$-$C_8$ alkenyl, $C_1$-$C_8$ alkynyl, halogenated $C_1$-$C_8$ alkanyl, and aryl substituted with Me, OMe, halide, OH, and R is CN, OH, $NH_2$, $C_1$-$C_8$ alkanyl, $C_1$-$C_8$ alkenyl, $C_1$-$C_8$ alkynyl, aryl, or $(CH_2)_m$-aryl where m is 1-10.

In one embodiment, a present compound may be combined with a pharmaceutically acceptable carrier or diluent to form a composition.

In one embodiment, the present invention provides a method for the treatment of sickle cell disease or a complication associated therewith in an individual who is in need thereof, comprising administering to the individual a compound in an amount effective for treatment of sickle cell disease or a complication associated therewith, wherein the compound is set forth above.

In one embodiment, the present invention provides a method for the treatment of a disease involving the migration of T-cells to the skin or a complication associated therewith in an individual who is in need thereof, comprising administering to the individual a compound in an amount effective for treatment of a disease involving the migration of T-cells to the skin or a complication associated therewith, wherein the compound is set forth above.

In one embodiment, the present invention provides a method for the treatment of acute myocardial infarction or a complication associated therewith in an individual who is in need thereof, comprising administering to the individual a compound in an amount effective for treatment of acute myocardial infarction or a complication associated therewith, wherein the compound is set forth above.

In one embodiment, the present invention provides a method for the treatment of a cancer involving a selectin or a complication associated therewith in an individual who is in need thereof, comprising administering to the individual a compound in an amount effective for treatment of a cancer involving a selectin or a complication associated therewith, wherein the compound is set forth above.

In other embodiments, the above compounds or compositions thereof may be used, and in the manufacture of a medicament, for any of the uses recited herein.

These and other aspects of the present invention will become apparent upon reference to the following detailed description and attached drawings. All references disclosed herein are hereby incorporated by reference in their entirety as if each was incorporated individually.

DETAILED DESCRIPTION

Figure 1A:
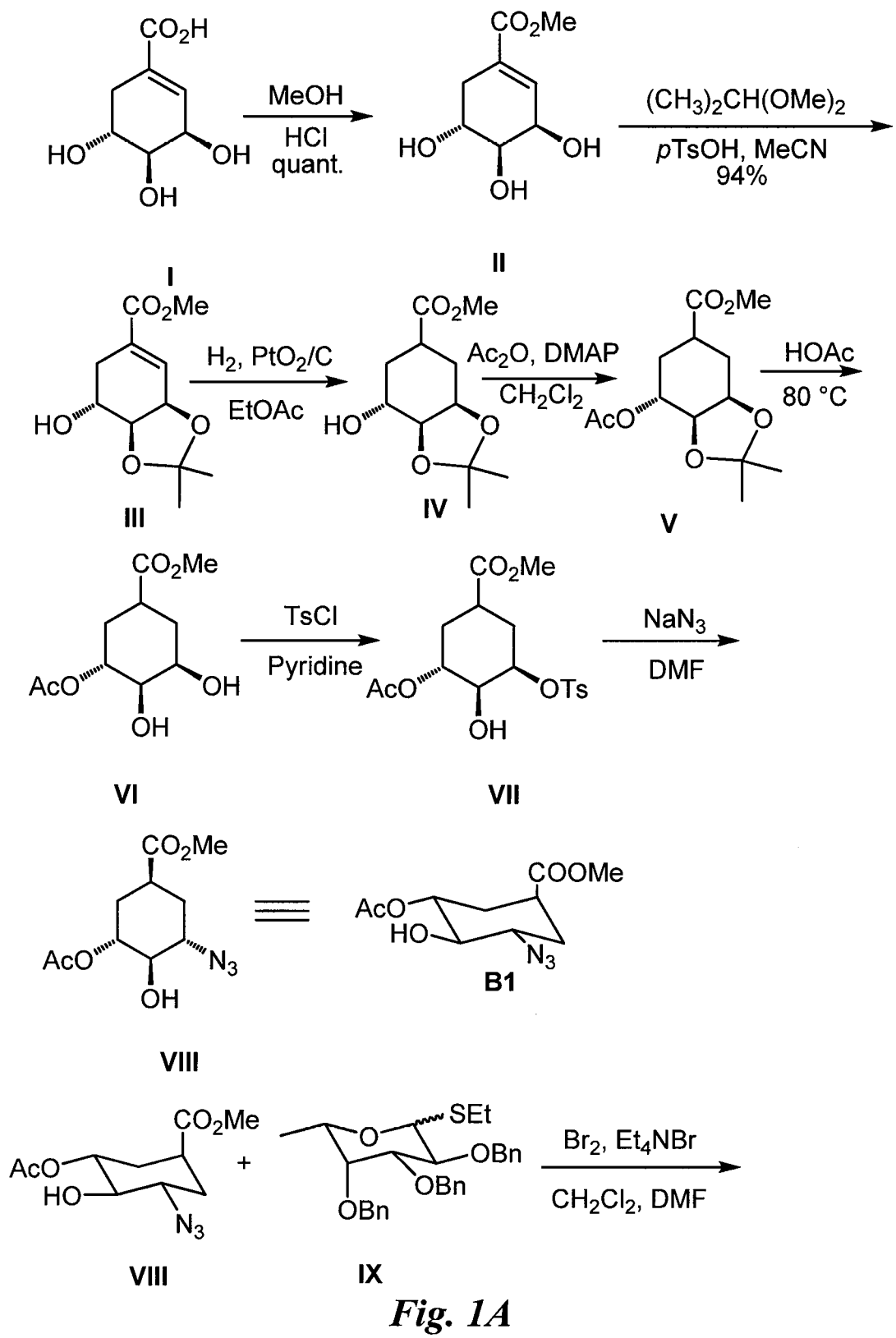
FIGS. 1A-1D are a diagram illustrating the synthesis of a glycomimetic.
Figure 1B:
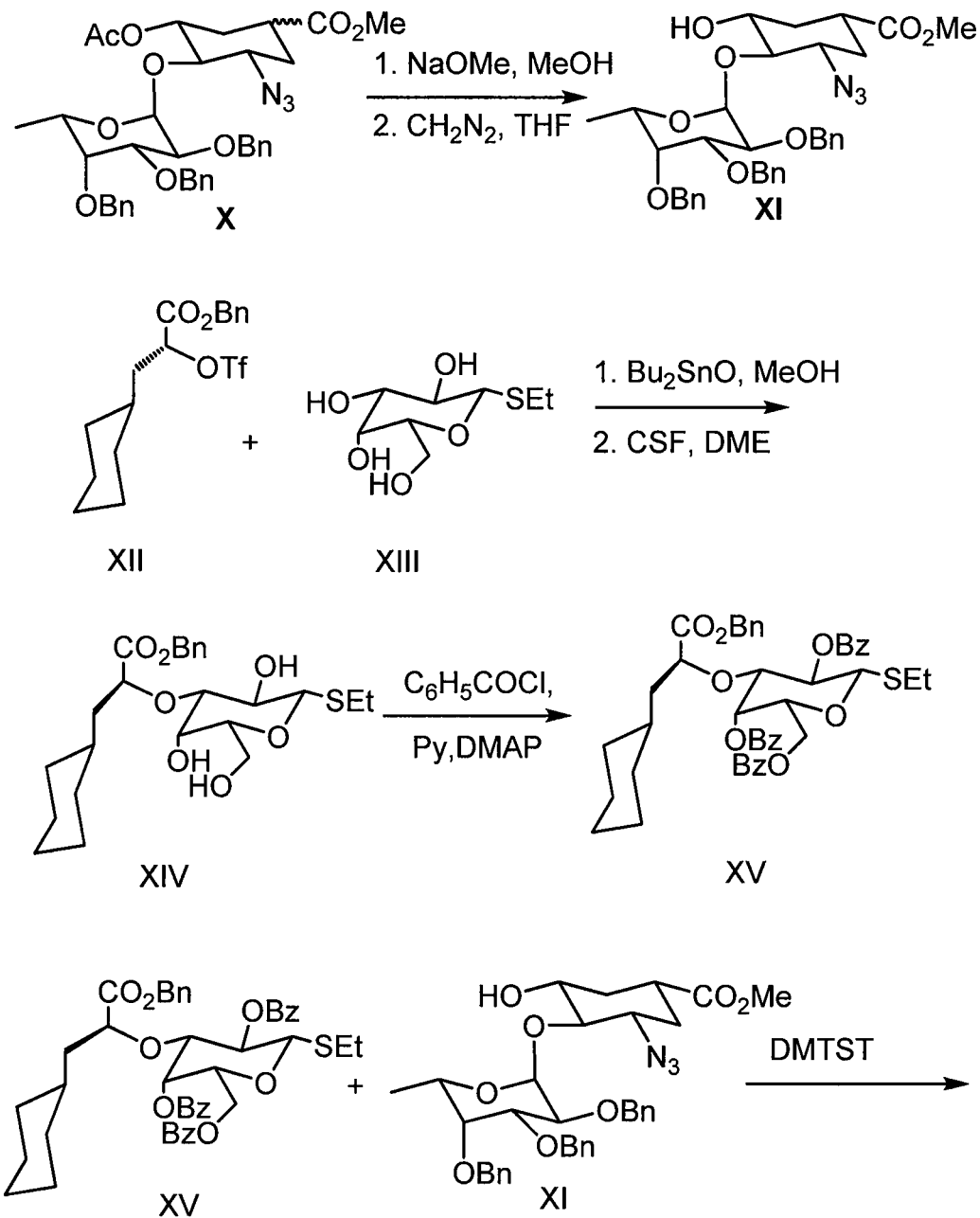
Figure 1C:
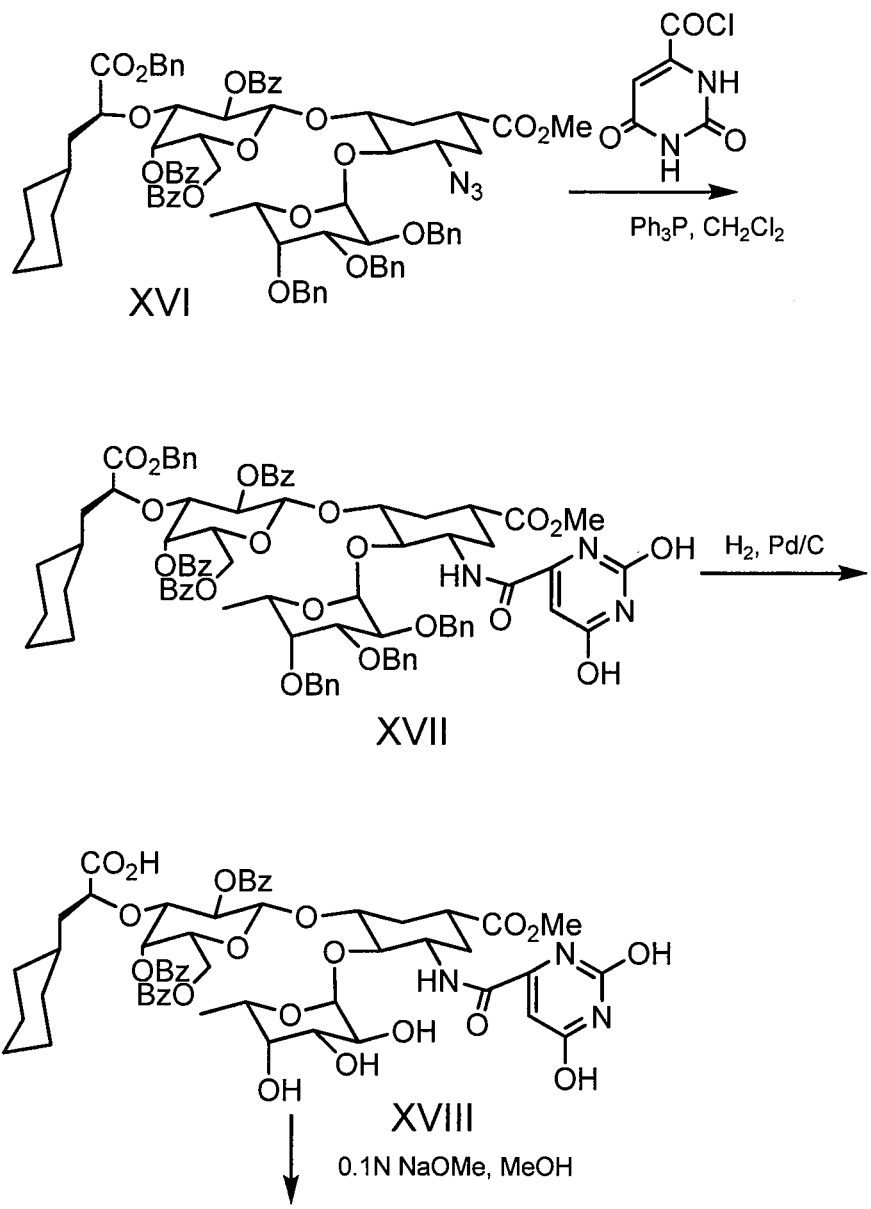
Figure 1D:
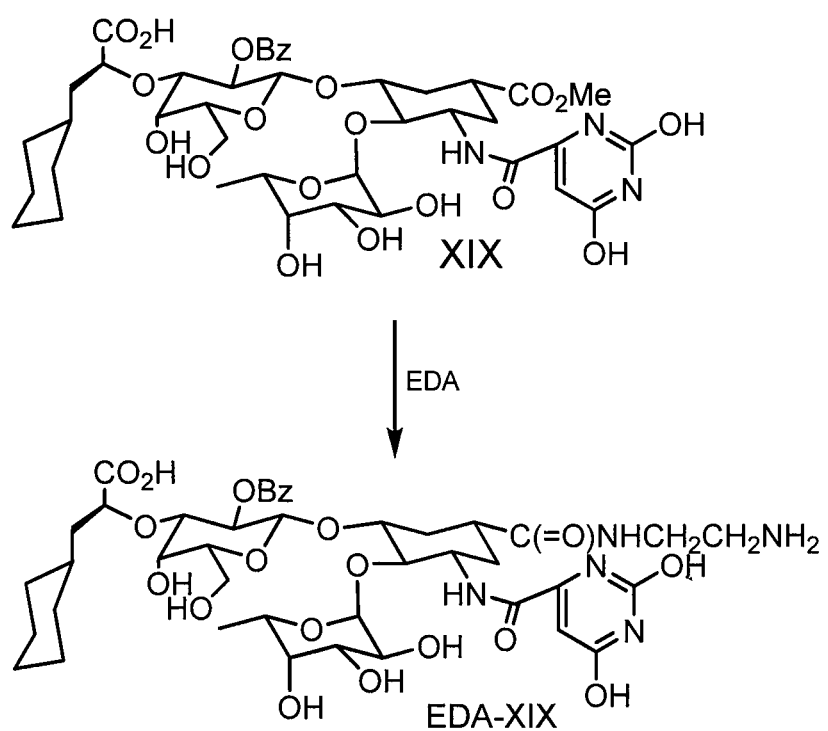

As noted above, the present invention provides compounds, compositions and methods for the treatment of diseases or complications associated therewith, in which a selectin plays a role in an individual. The compounds are inhibitors of selectins, and have a variety of uses in vitro and in vivo.

The present compounds have the formula:

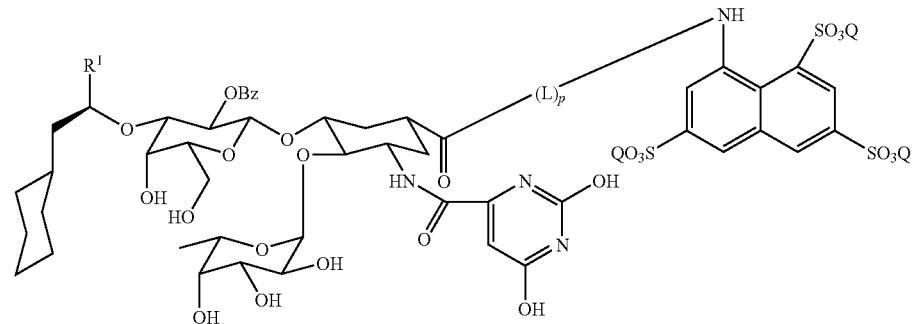

In the above formula and the present disclosure generally, there are several abbreviations. "Bz" is benzoyl. "Ar" is aryl.

"Et" is ethyl. "Me" is methyl. As any acids in the above formula may be in the form of a free acid or a salt, the various forms are encompassed by "Q" where denoted. "Q" is hydrogen (H) or a physiologically acceptable salt, unless defined otherwise herein. Examples of physiologically acceptable salts are Na, K, Li, Mg and Ca. Where groups may be present in multiples or not at all, the arbitrary letters "p", "n", "m" and "q" represent ranges of integers as defined herein. As used herein, the term "independently selected" refers to the selection of identical or different substituents.

In the above formula, "L" represents a linker which joins the carbon of C(=O) of the glycomimetic portion of the compound to NH of the diphenyl portion (i.e., to an aminonaphthalene trisulfonic acid). There may be no linkers present (i.e., "p" is 0) or a linker may be present (i.e., "p" is 1). Where no linker is present, the compound is with the formula:

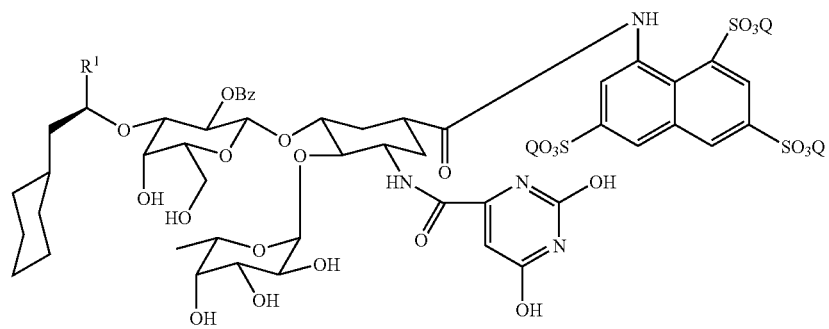

Where p is 1, a linker is present. A linker may include a spacer group, such as —(CH$_2$)$_q$— or —O(CH$_2$)$_q$— where q is generally about 1-20 (including any whole integer range therein). Other examples of spacer groups include a carbonyl or carbonyl containing group such as an amide.

Embodiments of linkers include the following:

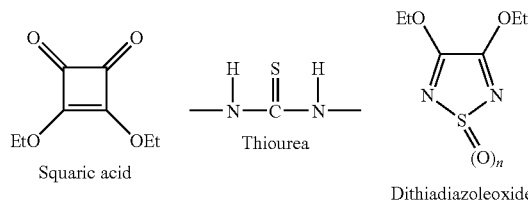

Other linkers, e.g., polyethylene glycols (PEG) or —C(=O)—NH—(CH$_2$)$_q$—C(=O)—NH$_2$ where q is as defined above, will be familiar to those in the art or in possession of the present disclosure.

In another embodiment, the linker is

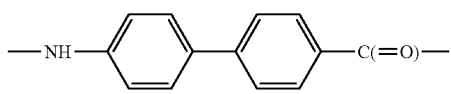

which produces:

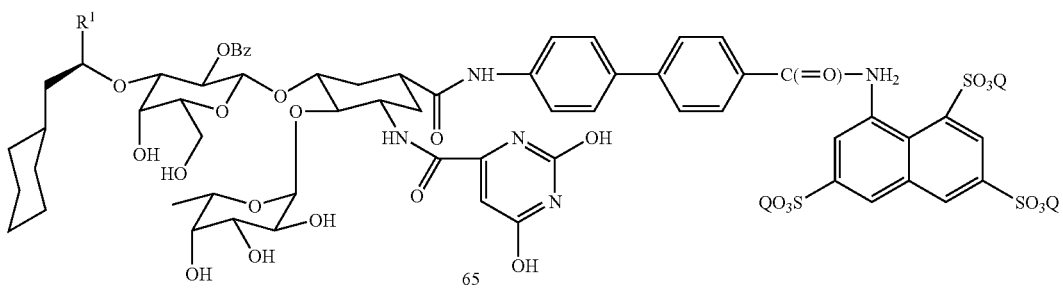

In another embodiment, the linker is
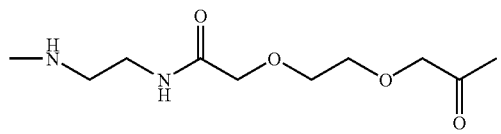 [SMILES: CNCCNC(=O)COCCOCC(C)=O]
which produces:
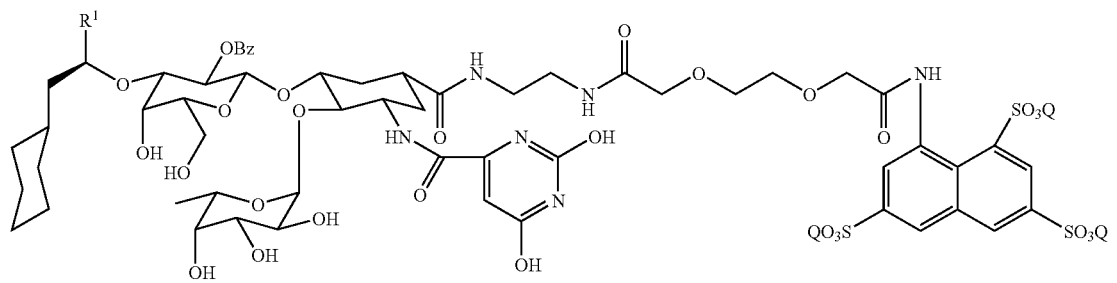
In another embodiment, the linker is
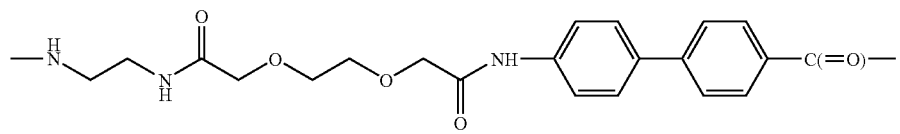
which produces:
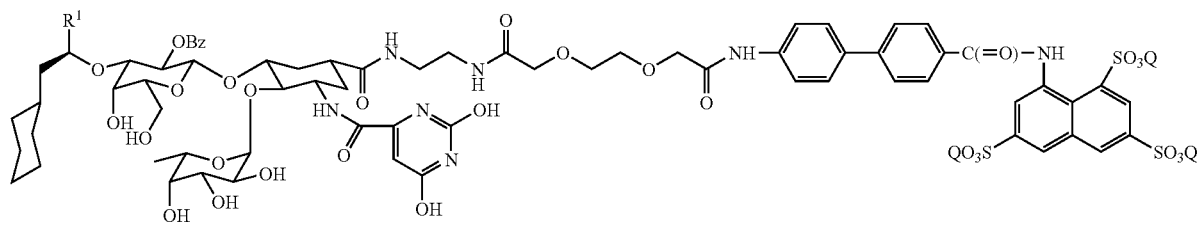
The present compounds, having the formula set forth above with $(L)_p$, possess the substituent "$R^1$". $R^1$ is one of
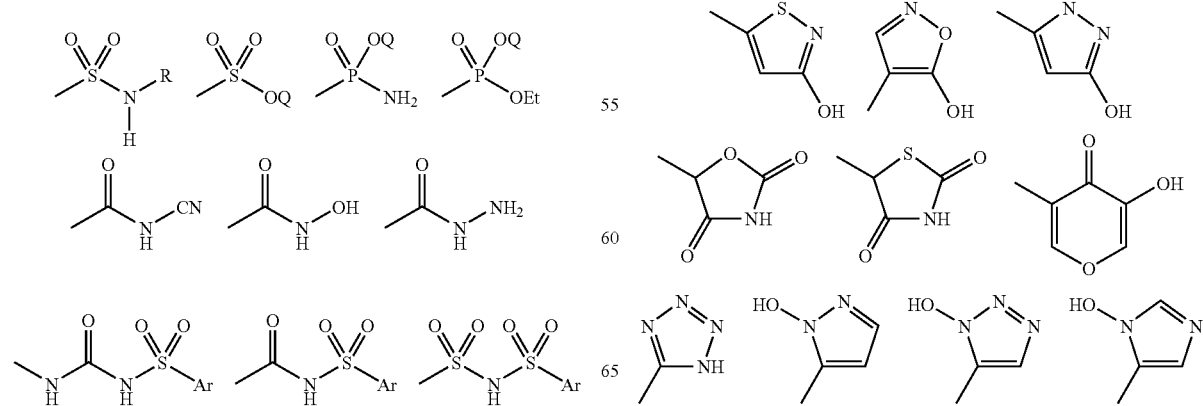
-continued
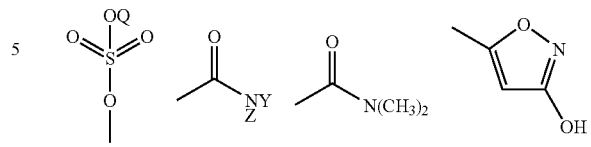

-continued

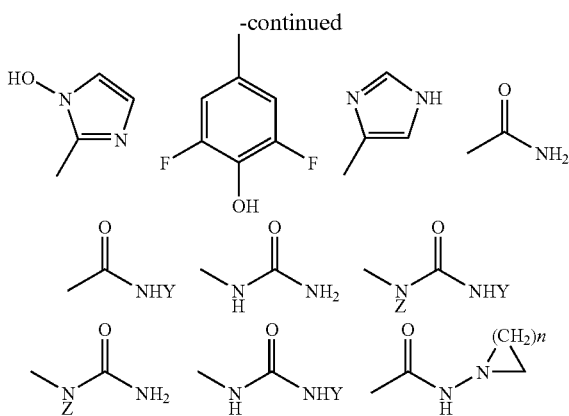

where Ar is aryl, Q is H, a physiologically acceptable salt, $C_1$-$C_8$ alkanyl, $C_1$-$C_8$ alkenyl, $C_1$-$C_8$ alkynyl, aryl, or $(CH_2)_m$-aryl where m is 1-10, n=1-4, and Z and Y are independently selected from $C_1$-$C_8$ alkanyl, $C_1$-$C_8$ alkenyl, $C_1$-$C_8$ alkynyl, halogenated $C_1$-$C_8$ alkanyl, and aryl substituted with Me, OMe, halide, OH, and R is CN, OH, $NH_2$, $C_1$-$C_8$ alkanyl, $C_1$-$C_8$ alkenyl, $C_1$-$C_8$ alkynyl, aryl, or $(CH_2)_m$-aryl where m is 1-10.

In an embodiment, $R^1$ is

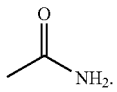

This embodiment applies to where the linker is $(L)_p$ or any of the specific linkers disclosed herein.

In another embodiment, $R^1$ is

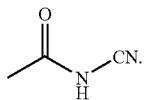

This embodiment applies to where the linker is $(L)_p$ or any of the specific linkers disclosed herein.

In another embodiment, $R^1$ is

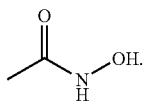

This embodiment applies to where the linker is $(L)_p$ or any of the specific linkers disclosed herein.

As used herein, a "$C_1$-$C_8$ alkanyl" refers to an alkane substituent with one to eight carbon atoms and may be straight chain, branched or cyclic (cycloalkanyl). Examples are methyl, ethyl, propyl, isopropyl, butyl and t-butyl. A "halogenated $C_1$-$C_8$ alkanyl" refers to a "$C_1$-$C_8$ alkanyl" possessing at least one halogen. Where there is more than one halogen present, the halogens present may be the same or different or both (if at least three present). A "$C_1$-$C_8$ alkenyl" refers to an alkene substituent with one to eight carbon atoms, at least one carbon-carbon double bond, and may be straight chain, branched or cyclic (cycloalkenyl). Examples are similar to "$C_1$-$C_8$ alkanyl" examples except possessing at least one carbon-carbon double bond. A "$C_1$-$C_8$ alkynyl" refers to an alkyne substituent with one to eight carbon atoms, at least one carbon-carbon triple bond, and may be straight chain, branched or cyclic (cycloalkynyl). Examples are similar to "$C_1$-$C_8$ alkanyl" examples except possessing at least one carbon-carbon triple bond. An "alkoxy" refers to an oxygen substituent possessing a "$C_1$-$C_8$ alkanyl," "$C_1$-$C_8$ alkenyl" or "$C_1$-$C_8$ alkynyl." This is —O-alkyl; for example methoxy, ethoxy, n-propoxy, i-propoxy, n-butoxy and the like; and alkenyl or alkynyl variations thereof (except for methoxy). It further refers to the group O-alkyl-W-alkyl where W is O or N; for example —O—$(CH_2)_n$—W—$(CH_2)_m$ where n and m are independently 1-10. An "aryl" refers to an aromatic substituent with one to fourteen carbon atoms as ring atoms in one or multiple rings which may be separated by a bond or fused. As used herein, "aryl" includes "heteroaryl." A "heteroaryl" is similar to an "aryl" except the aromatic substituent possesses at least one heteroatom (such as N, O or S) in place of a ring carbon. Where an aromatic substituent is an aryl in which all the ring atoms are carbon (i.e., not a heteroaryl), there are typically six to fourteen ring atoms. Where an aryl is a heteroaryl, there may be less than six carbon ring atoms. Examples of aryls include phenyl, naphthyl, pyridinyl, pyrimidinyl, triazolo, furanyl, oxazolyl, thiophenyl, quinolinyl and diphenyl.

The following confirms what would be understood by one of skill in the art in possession of the present disclosure. The line to which no element is attached at one end of any $R^1$ substituent disclosed herein is intended to be the same line (i.e., the same bond) that joins $R^1$ in any of the compound formula depicted above.

All compounds of the present invention or useful thereto (e.g., for pharmaceutical compositions or methods of treating), include physiologically acceptable salts thereof. Examples of such salts are Na, K, Li, Mg, Ca and Cl.

Compounds as described herein may be present within a pharmaceutical composition. A pharmaceutical composition comprises one or more compounds in combination with (i.e., not covalently bonded to) one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. Compositions of the present invention may be formulated for any appropriate manner of administration, including for example, topical, oral, nasal, intravenous, intracranial, intraperitoneal, subcutaneous, or intramuscular administration.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of compound release. The amount of compound contained within a sustained release formulation depends upon the site of implantation, the rate and expected duration of release and the nature of the condition to be treated.

The above described compounds including equivalents thereof are useful in methods of the present invention to treat individuals in need thereof. As used herein, such individuals include humans, as well as non-human warm-blooded animals such as non-human mammals. A preferred individual for treatment is a human. Typically a compound will be administered to an individual as a pharmaceutical composition, i.e., in combination with a pharmaceutically acceptable carrier or diluent.

In an embodiment, an individual who is in need of treatment for sickle cell disease or a complication associated therewith is administered at least one (i.e., one or more) of the above described compounds in an amount effective for the treatment. As used herein, the term "treatment" (including variations such as "treating") includes prevention. For example, a complication associated with sickle cell disease may not have presented itself in an individual with the disease, and a compound may be administered to prevent presentation of the complication in the individual. Sickle cell disease and complications associated therewith include, for example, anemia, red blood cells becoming stuck in blood vessels, ischemia, infarction, stroke, acute chest crisis, splenic sequestration crisis, shortened life expectancy, organ damage and periodic or chronic pain.

In an embodiment, an individual who is in need of treatment for a disease involving the migration of T-cells to the skin or a complication associated therewith is administered at least one (i.e., one or more) of the above described compounds in an amount effective for the treatment. Examples of diseases involving the migration of T-cells to the skin include atopic dermatitis, psoriasis, cutaneous T-cell lymphoma, and graft vs. host disease following bone marrow transplantation. Complications associated with diseases involving the migration of T-cells to the skin include redness of the skin, swelling of the skin, and accumulation of T-cells or T-cell lymphomas in the skin.

In an embodiment, an individual who is in need of treatment for acute myocardial infarction or a complication associated therewith is administered at least one (i.e., one or more) of the above described compounds in an amount effective for the treatment. An acute myocardial infarction includes those that are post ischemia or post reperfusion. Complications associated with acute myocardial infarction include chest pain, shortness of breath and syncope.

In an embodiment, an individual who is in need of treatment for a cancer involving a selectin or a complication associated therewith is administered at least one (i.e., one or more) of the above described compounds in an amount effective for the treatment. Complications associated with a cancer involving a selectin include shortened life expectancy, organ damage, and periodic or chronic pain.

The term "treatment," as set forth above, refers to any of a variety of positive effects from the treatment including, for example, eradicating a complication associated with the disease, relieving to some extent a complication, slowing or stopping progression of the disease, and prolonging the survival time of the recipient. The treatment may be used in conjunction with one or more other therapies for any of the illnesses (or complications associated therewith) described above.

The above described compounds may be administered in a manner appropriate to the disease to be treated. Appropriate dosages and a suitable duration and frequency of administration may be determined by such factors as the condition of the patient, the type and severity of the patient's disease and the method of administration. In general, an appropriate dosage and treatment regimen provides the compound(s) in an amount sufficient to provide therapeutic and/or prophylactic benefit. Within particularly preferred embodiments of the invention, a compound may be administered at a dosage ranging from 0.001 to 1000 mg/kg body weight (more typically 0.01 to 1000 mg/kg), on a regimen of single or multiple daily doses. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated, which will be familiar to those of ordinary skill in the art.

The following Examples are offered by way of illustration and not by way of limitation.

EXAMPLES

Example 1

Synthesis of Glycomimetic (FIG. 1)

Synthesis of Intermediate II:
(−)-Shikimic acid (20 g) in MeOH (200 ml) and sulfuric acid (2 ml, 98%) are stirred at room temperature (rt) for 50 h. The reaction mixture is neutralized with 2N aqueous NaOH in the cold. After evaporation to dryness, the residue is purified by silica gel chromatography to afford II (19.2 g).

Synthesis of Intermediate III:
Methyl shikimate (II, 10 g), 2,2-dimethoxypropane (10 ml) and p-TsOH (0.8 g) are dissolved in acetonitrile (125 ml) and stirred at rt for 1 h. The reaction mixture is then neutralized with triethylamine (2 ml) and evaporated to dryness. The residue is chromatographed on silica gel to yield III (11 g).

Synthesis of Intermediate IV:
The shikimic acid derivative III (10 g) and $PtO_2/C$ (10%, 250 mg) in MeOH (40 ml) are hydrogenated at rt under vigorous stirring. After 16 h the reaction mixture is filtered over celite and evaporated to dryness. The residue is chromatographed on silica gel to yield IV (8.6 g).

Synthesis of Intermediate V:
To a solution of IV (8 g) in DCM (100 ml) at 0° C. are added pyridine (12 ml), acetic anhydride (7 ml) and a DMAP (25 mg). The reaction mixture is stirred at rt for 1 h, and diluted with EtOAc (250 ml). After washing with 0.5 M aqueous HCl (3×50 ml), saturated solution of $KHCO_3$ (3×50 ml) and brine (3×50 ml), the combined organic layers are dried ($Na_2SO_4$) and evaporated to dryness. The residue is purified by chromatography on silica gel to yield V (6.8 g).

Synthesis of Intermediate VI:
A solution of V (6.0 g) in acetic acid (30 ml, 80%) is stirred at 80° C. for 1 h. Solvent is evaporated off and the residue is purified by chromatography on silica gel (DCM/MeOH 14:1) to yield VI (3.6 g).

Synthesis of Intermediate (VII):
A solution of VI (3 g) and p-TsCl (3.5 g) in pyridine (30 ml) is stirred at rt for 6 h. MeOH (5 ml) is added and the solvent is evaporated at reduced pressure, the residue dissolved in EtOAc (3×150 ml) and the organic layers are washed with 0.5 M aqueous HCl (0° C.), water (cold) and brine (cold). The combined organic layers are dried ($Na_2SO_4$), filtered on Celite and evaporated to dryness. The residue is purified by chromatography on silica gel (toluene/EtOAc 4:1) to yield VII (3.7 g).

Synthesis of Compound VIII:
A solution of VII (3 g) and $NaN_3$ (2.5 g) in DMF (20 ml) is stirred at 80° C. The reaction mixture is cooled to rt and diluted with EtOAc (200 ml) and water (50 ml). The organic layer is additionally washed twice with water (2×50 ml) and once with brine (50 ml). All aqueous layers are extracted twice with EtOAc (2×50 ml). The combined organic layers are dried with $Na_2SO_4$, filtered and the solvent is evaporated off. The residue is purified by chromatography on silica gel (petroleum ether/EtOAc 5:2) to give VIII (2.2 g).

Synthesis of Compound X:

To a solution of ethyl 2,3,4-tri-O-benzyl-α-L-fucothiopyanoside IX (1.5 g) in DCM (3 ml), bromine (150 µl) is added at 0° C. under argon. After 5 min the cooling bath is removed and the reaction mixture is stirred for an additional 25 min at rt. Cyclohexene (200 µl) is added and the reaction mixture is added to a solution of VIII (400 mg), $(Et)_4NBr$ (750 mg) and powdered 4 Å molecular sieves in DCM (10 ml) and DMF (5 ml). After 16 h, triethylamine (1.5 ml) is added and stirred for an additional 10 min, diluted with EtOAc (50 ml) and washed with sat. aqueous $NaHCO_3$, water and brine. The aqueous layers are extracted twice with EtOAc (2×50 ml). The combined organic layers are dried ($Na_2SO_4$), filtered and evaporated to dryness. The residue is purified by chromatography on silica gel (toluene/EtOAc 9:1) to yield X (700 mg).

Synthesis of Compound XI:

To a solution of X (1.5 g) in MeOH (20 ml) is added freshly prepared NaOMe (80 mg) and the reaction mixture is stirred in a pressure tube at 80° C. for 20 h. The reaction mixture is cooled to rt and neutralized with acetic acid. Solvent is evaporated to dryness and the residue is dissolved in ether. Freshly prepared diazomethane is added and the excess diazomethane is neutralized with acetic acid. Solvent is evaporated off to give XI (1.25 g).

Synthesis of Building Block XV:

This synthesis is done exactly in same way as described previously (*Helvetica Chemica Acta* 83:2893-2907 (2000)).

Synthesis of Compound XVI:

A mixture of XI (1.6 g), XV(3 g) and activated powdered molecular sieves 4 Å (1 g) in DCM (17 ml) is stirred at rt under argon for 2 h. Then DMTST (2 g) is added in 4 equal portions over a period of 1.5 h. After 24 h the reaction mixture is filtered over Celite and the filtrate is diluted with DCM (100 ml). The organic layer is washed with sat. aqueous $NaHCO_3$ and brine and the aqueous layers are extracted twice with DCM. The combined organic layers are dried ($Na_2SO_4$), filtered and evaporated to dryness. The residue is purified by chromatography on silica gel (toluene/EtOAc 8:1) to yield XVI (1.5 g).

Synthesis of Compound XVII:

To a solution of XVI (500 mg) and orotic acid chloride (500 mg) in dichloromethane (10 ml) is added a solution of triphenylphosphine (500 mg in 5 ml dichloromethane) dropwise during 10 min. The reaction mixture is stirred at rt for 25 h and the solvent is evaporated off. The residue is purified (chromatography on silica gel DCM/MeOH 19:1) to give XVII (250 mg).

Synthesis of Compound XVIII: To a solution of XVII (200 mg) in dioxane-water (5:1, 12 ml) is added 10% Pd—C (100 mg) and the reaction mixture is stirred vigorously under hydrogen (55 psi) for 24 h. Catalyst is filtered through a bed of celite and the solvent is evaporated off. Residue is purified by silica gel chromatography to give compound XVIII (150 mg).

Synthesis of XIX:

To a solution of compound XVIII (145 mg) in MeOH (5 ml) is added a solution of NaOMe in MeOH (25%, 0.025 ml) and the reaction mixture is stirred at rt for 4 h, neutralized with acetic acid and the solvent is evaporated off. Residue is dissolved in water and passed through a bed of Dowex 50wX-8 (Na-form) resin. Water wash is evaporated off to afford compound XIX (100 mg).

Synthesis of EDA-XIX:

XIX (80 mg) is heated at 70° C. with ethylenediamine (EDA) (1 ml) with stirring for 5 h. Solvent is evaporated off and then purified by sephadex G-25 column to give EDA-XIX (82 mg).

Example 2

Figure 2:
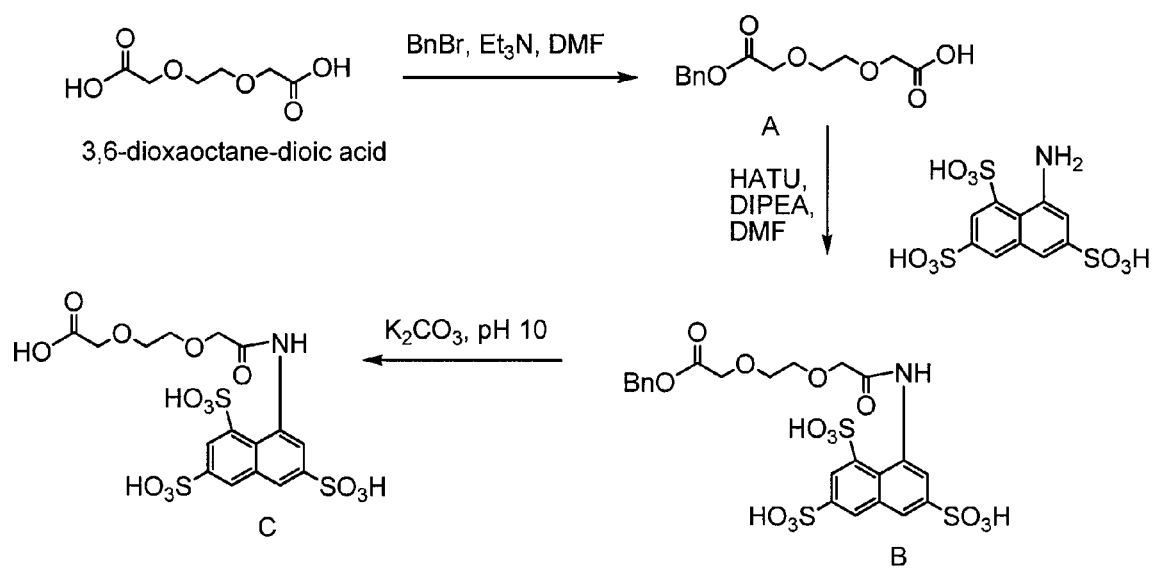
FIG. 2 is a diagram illustrating the synthesis of aminonaphthalene trisulfonic acid with linker.

Synthesis of Aminonaphthalene Trisulfonic Acid with Linker (FIG. 2)

Synthesis of Intermediate A:

To a solution of 3,6-dioxaoctanedioic acid (4.34 g) in DMF (220 ml) is added triethylamine (6.2 ml) and cooled to 0° C. To this solution is added a solution of benzyl bromide (2.4 ml) in DMF (220 ml) dropwise with stirring over a 2 h period at 0° C. and continued to stir at the same temperature for 4 h. After 4 h, the reaction mixture is slowly warmed to room temperature and stirred at room temperature for overnight. Solvent is removed under reduced pressure and the residue is dissolved in 1M HCl in saturated NaCl solution (500 ml). The aqueous solution is extracted with EtOAc (6×200 ml). The combined organic extracts are dried ($Na_2SO_4$) and concentrated to dryness. The residue is purified by flush chromatography to give compound A (2 g).

Synthesis of Intermediate B:

To a solution of compound A (1 g) in DMF (10 ml) is added diisopropylethylamine (0.45 ml) and then HATU (1.2 g). A solution of 8-aminonaphthalene-1,3,6-trisulfonic acid (1.5 g) in DMF (10 ml) and diisopropylethylamine (0.45 ml) is added to the above solution after 5 min with stirring. The reaction mixture is stirred at room temperature for 1 h. The solvent is evaporated off under reduced pressure and the residue is purified by reversephase (C-18) column to give compound B (0.5 g).

Synthesis of Compound C:

Compound B (0.5 g) is dissolved in an aqueous solution of $K_2CO_3$ and the pH of the solution is adjusted to 10 by adding 1N solution of NaOH with stirring. The reaction mixture is stirred at room temperature for 1 h, neutralized to pH 7 with 1N HCl, solvent is evaporated off and the residue is purified on a sephadex G-10 column to give compound C (0.2 g).

Example 3

Figure 3:
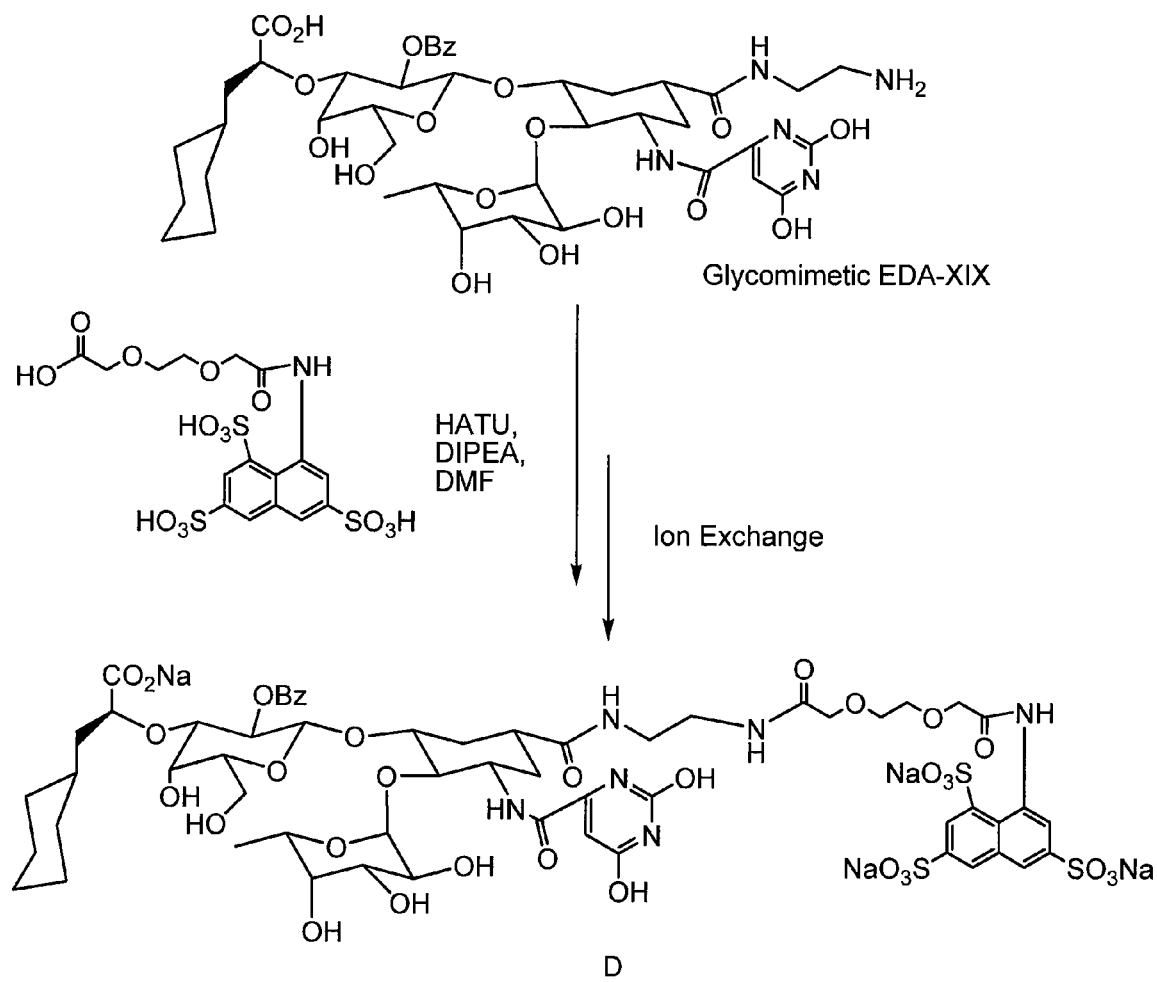
FIG. 3 is a diagram illustrating the synthesis of a compound formed by coupling the compound of FIG. 1D with the compound of FIG. 2.

Synthesis of Compound D (FIG. 3)

EDA-XIX (Example 1) and compound C (Example 2) are each co-evaporated once with DMF separately. Compound C (421 mg, 0.452 mmol) is dissolved in 5 mL of anhydrous DMF at rt. To the compound C solution is added 400 µL (2.3 mmol) of DIPEA followed by 154 mg (0.406 mmol) of HATU. The reaction solution is stirred at rt for 5 min. EDA-XIX (208 mg, 0.226 mmol) is partially dissolved in 5 mL of anhydrous DMF. The compound C reaction solution is transferred to the EDA-XIX mixture at rt. The compound C reaction flask is rinsed with an additional 5 mL of anhydrous DMF and the solution is transferred to the EDA-XIX reaction flask. After stirring for 1 hr at rt, the reaction is concentrated in vacuo. The resulting yellow residue is dissolved in $dH_2O$ and purified on a Waters SepPak C18 (5 g) cartridge. The C18 cartridge is eluted with $dH_2O$ (3×80 mL), 10% MeOH in $dH_2O$ (1×80 mL), 20% MeOH in $dH_2O$ (2×80 mL), 30% MeOH in $dH_2O$ (1×80 mL) and 50% MeOH in $dH_2O$ (1×80 mL). All fractions containing methanol are concentrated separately and further purified by HPLC using a Gemini C18 column (Phenomenex) using 10 mM NH₄Ac and CH₃CN mixture as mobile phase to give compound D as ammonium salt. Compound D is further converted to Na-salt form by passing through a column of ion-exchange resin (IR-120 sodium form). Yield 150 mg.

Example 4

Figure 4A:
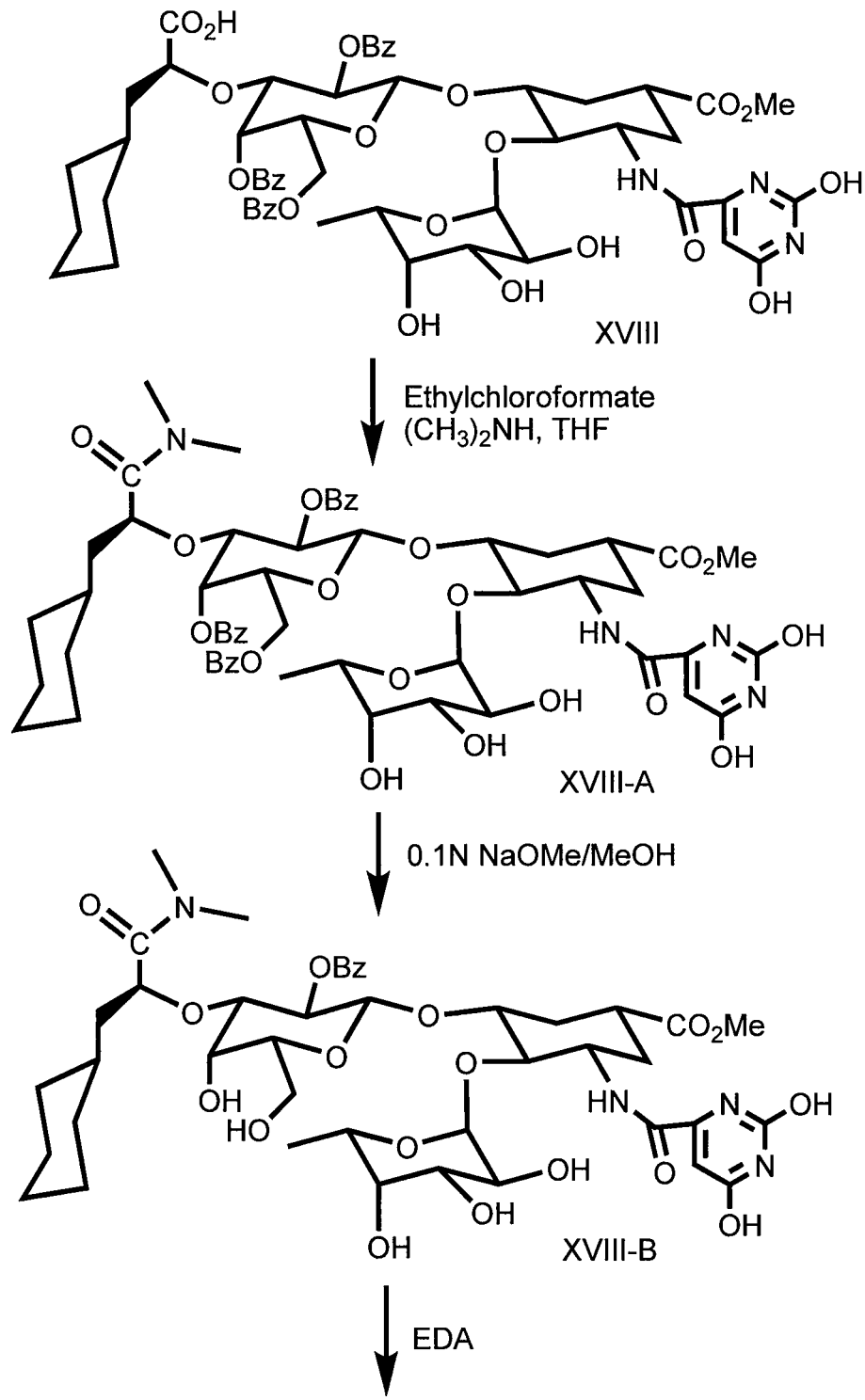
FIGS. 4A-4B are a diagram illustrating the modification of the compound of FIG. 3 (beginning with compound XVIII of FIG. 1C and using compound C of FIG. 2), whereby the —COOH group is converted to a substituent selected from $R^1$ as defined herein.
Figure 4B:
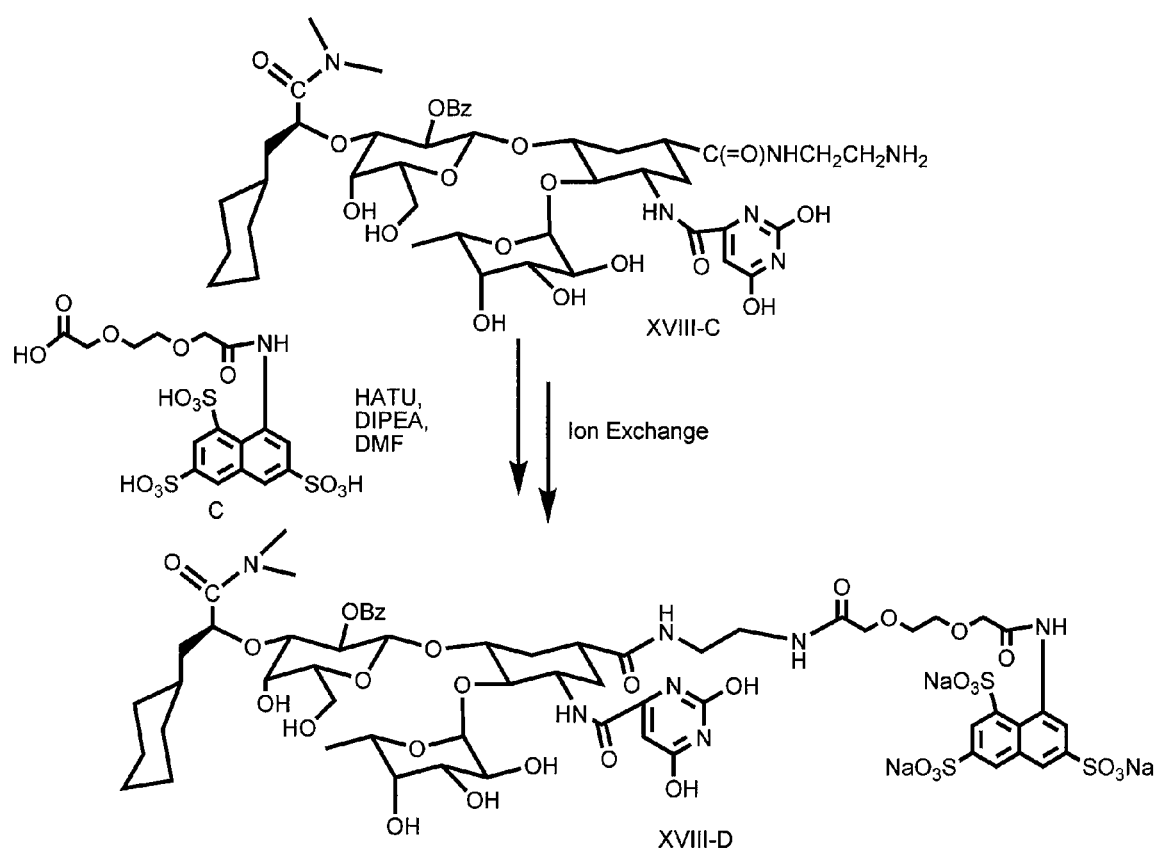
Figure 5:
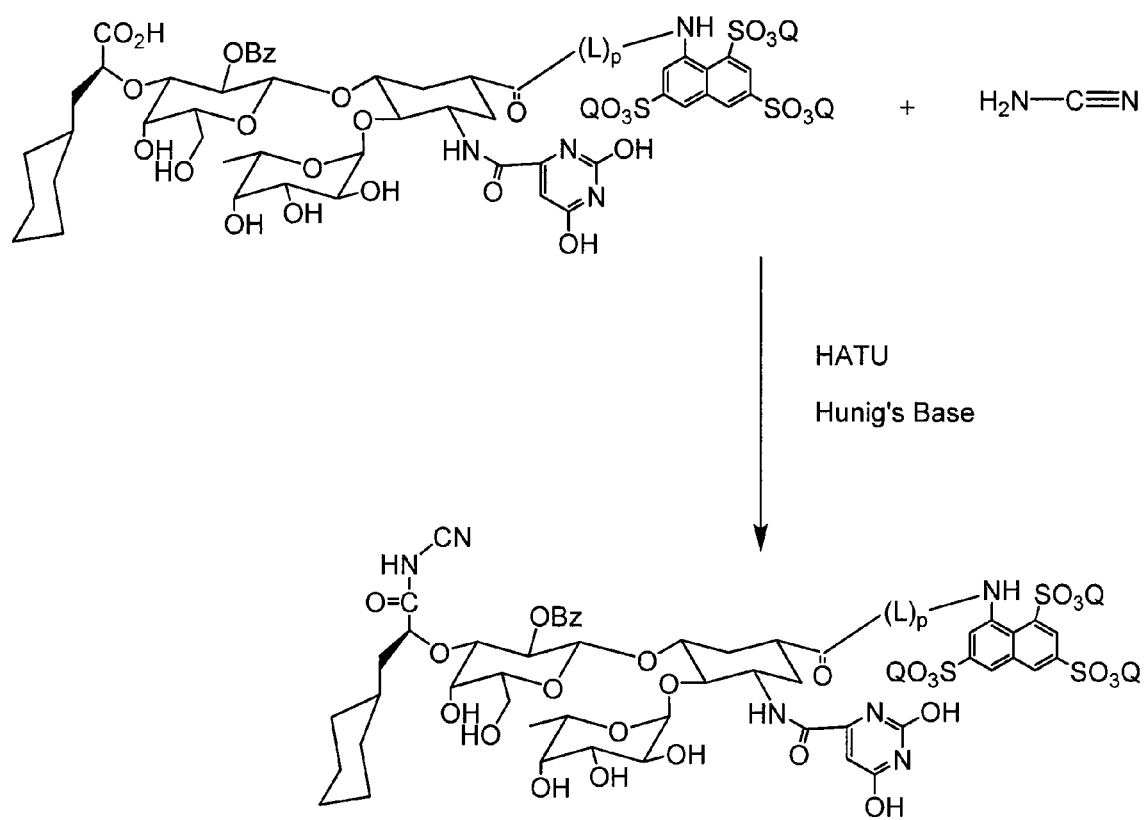
FIG. 5 is a diagram illustrating the modification of a compound such as the compound of FIG. 3, whereby the —COOH group is converted to a substituent selected from $R^1$ as defined herein.

Synthesis of Compound XVIII-D (FIG. 4)

Synthesis of Intermediate XVIII-A:

To a cool (5° C.) solution of XVIII (100 mg) (Example 1) in THF (0.8 ml) is added triethylamine (0.025 ml) and ethylchloroformate (0.014 ml) under argon. The reaction mixture is stirred for 15 min in the cold and the ice-bath is removed. A solution (2 M) of (CH₃)₂NH in THF (0.07 ml) is added and stirred for 1 h at room temperature. The reaction mixture is evaporated to dryness and purified by column chromatography (silica gel) to give compound XVIII-A (55 mg).

Synthesis of Intermediate XVIII-B:

Compound XVIII-A (50 mg) is stirred at room temperature with a 0.1N solution of NaOMe in MeOH (1 ml) for 3 h. AcOH (0.02 ml) is added with stirring and the solvent is evaporated to dryness. Solid residue is purified by column chromatography (silica gel) to give intermediate XVIII-B (32 mg).

Synthesis of Intermediate XVIII-C:

Compound XVIII-B (30 mg) is dissolved in ethylenediamine (0.25 ml) and heated with stirring for 5 h at 70° C. Solvent is evaporated off and the residue is purified by reverse phase (sep-pak C18) chromatography to give compound XVIII-C (20 mg).

Synthesis of Compound XVIII-D:

Compound XVIII-C (15 mg) is treated with compound C (10 mg) (Example 2) exactly in the same way as described for compound D (Example 3) and the crude reaction mixture is purified and converted to Na-salt form exactly in the same way as described for compound D (Example 3) to give compound XVIII-D (10 mg).

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

From the foregoing it will be appreciated that, although specific embodiments of the invention have been described herein for purposes of illustration, various modifications may be made without deviating from the spirit and scope of the invention.

The invention claimed is:

1. A compound having the formula:

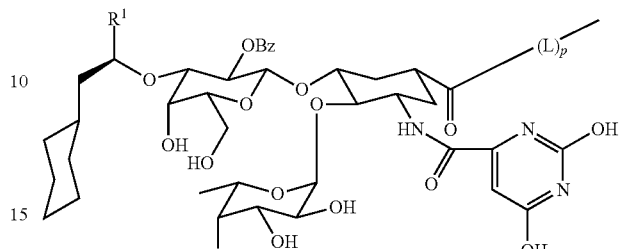

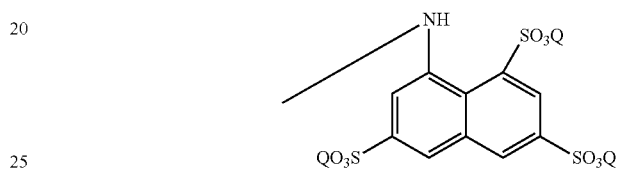

wherein
Bz=benzoyl;
L=linker group;
p=0-1; and
R¹ is selected from:

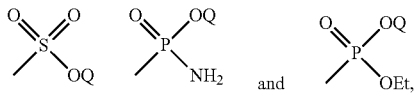

wherein each Q is independently selected from H and a physiologically acceptable salt.

2. The compound according to claim 1, wherein in the compound p=0.

3. The compound according to claim 1, wherein in the compound p=1 and L is

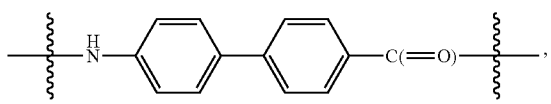

where the terminal N of L is attached to terminal C of C(=O) of the compound, and wherein the compound has the formula:

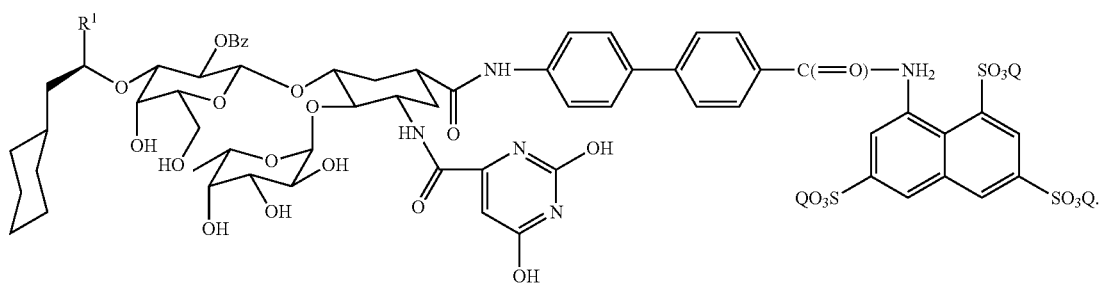

4. The compound according to claim 1, wherein in the compound p=1 and L is

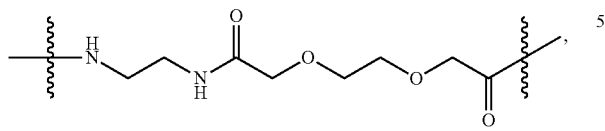

where the terminal N of L is attached to terminal C of C(=O) of the compound, and wherein the compound has the formula:

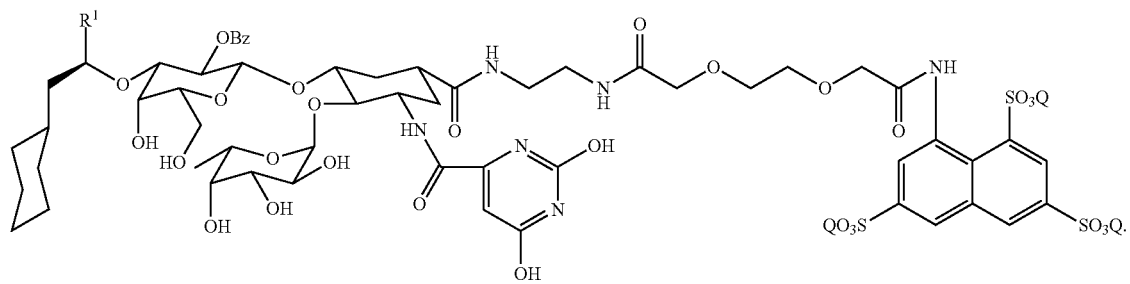

5. The compound according to claim 1, wherein in the compound p=1 and L is

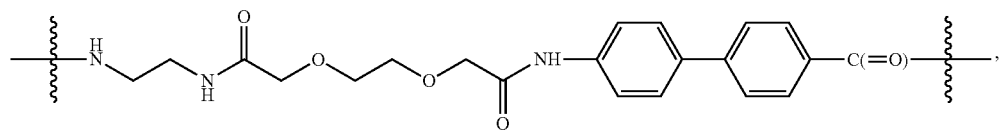

where the terminal N of L is attached to terminal C of C(=O) of the compound, and wherein the compound has the formula:

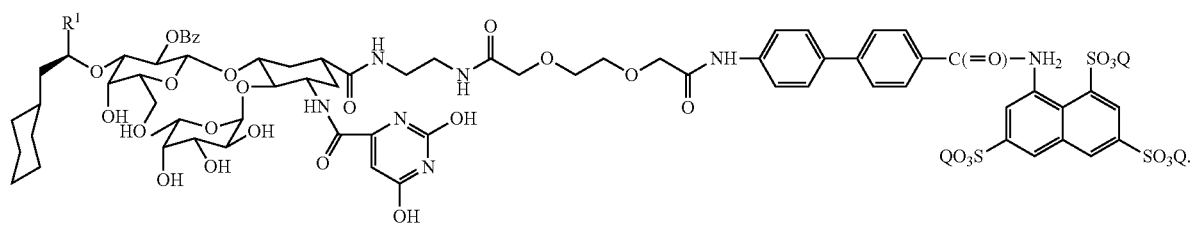

6. The compound according to claim 1, wherein the compound is in combination with a pharmaceutically acceptable carrier or diluent.

7. A method for the treatment of sickle cell disease or a complication associated therewith in an individual who is in need thereof, comprising administering to the individual a compound in an amount effective for treatment, wherein the compound is according to claim 1.

8. The method according to claim 7 wherein the compound is according to claim 2.

9. The method according to claim 7 wherein the compound is according to claim 3.

10. The method according to claim 7 wherein the compound is according to claim 4.

11. The method according to claim 7 wherein the compound is according to claim 5.

12. The method according to claim 7 wherein the compound is in combination with a pharmaceutically acceptable carrier or diluent.

13. The compound according to any one of claims 1-5, wherein the physiologically acceptable salt is a sodium salt.

* * * * *